US012746284B2

(12) United States Patent
Lee et al.

(10) Patent No.: US 12,746,284 B2
(45) Date of Patent: Sep. 29, 2026

(54) IMMUNE ADJUVANT AND VACCINE COMPOSITION INCLUDING THE SAME

(71) Applicant: REPUBLIC OF KOREA (ANIMAL AND PLANT QUARANTINE AGENCY), Gimcheon-si (KR)

(72) Inventors: Minja Lee, Yangsan-si (KR); Hyundong Jo, Gimcheon-si (KR); Su-Mi Kim, Jung-gu (KR); Byounghan Kim, Seocho-gu (KR); Jong-Hyeon Park, Gimcheon-si (KR)

(73) Assignee: REPUBLIC OF KOREA (ANIMAL AND PLANT QUARANTINE AGENCY), Gimcheon-si (KR)

( * ) Notice: Subject to any disclaimer, the term of this patent is extended or adjusted under 35 U.S.C. 154(b) by 830 days.

(21) Appl. No.: 18/002,231

(22) PCT Filed: Jun. 26, 2020

(86) PCT No.: PCT/KR2020/008364
§ 371 (c)(1),
(2) Date: Dec. 16, 2022

(87) PCT Pub. No.: WO2021/261635
PCT Pub. Date: Dec. 30, 2021

(65) Prior Publication Data

US 2023/0226176 A1 Jul. 20, 2023

(51) Int. Cl.
*A61K 39/00* (2006.01)
*A61K 39/12* (2006.01)
*A61K 39/135* (2006.01)
*A61K 39/39* (2006.01)
*A61P 37/04* (2006.01)

(52) U.S. Cl.
CPC .............. *A61K 39/39* (2013.01); *A61K 39/00* (2013.01); *A61K 39/135* (2013.01); *A61P 37/04* (2018.01); *A61K 2039/55511* (2013.01); *A61K 2039/55572* (2013.01)

(58) Field of Classification Search
CPC .......... A61K 2039/555; A61K 2039/57; A61K 39/00; A61K 39/135; A61K 39/39
See application file for complete search history.

(56) References Cited

U.S. PATENT DOCUMENTS

| | | | |
|---|---|---|---|
| 2007/0218086 | A1 | 9/2007 | Tiollier |
| 2009/0196887 | A1 | 8/2009 | Morita et al. |
| 2018/0326038 | A1 | 11/2018 | Rieder et al. |

FOREIGN PATENT DOCUMENTS

| | | | | |
|---|---|---|---|---|
| JP | 2003-160492 | A | | 6/2003 |
| JP | 2003-238409 | A | | 8/2003 |
| JP | 2005-500336 | A | | 1/2005 |
| JP | 2007-534743 | A | | 11/2007 |
| JP | 2009-507030 | A | | 2/2009 |
| KR | 10-2017-0042802 | A | | 4/2017 |
| KR | 10-2285977 | B1 | | 8/2021 |
| KR | 10-2022-0106945 | A | | 8/2022 |
| WO | 2003/009812 | A2 | | 7/2002 |
| WO | WO2016040369 | | * | 3/2016 |

OTHER PUBLICATIONS

Emerson et al, Overcoming Tumor-Induced imune suppression: From reliveing inhibition to providing costimulation with T cell agonists, BioDrugs, 2018, 32:221-231.*

Downey et al., "MAIT cells as attractive vaccine targets", FEBS Letter, 2019, 593:1627-1640).*

Patch et al., "Induction of foot-and-mouth disease virus-specific cytotoxic T cell killing by vaccination", Clinical and Vaccine Immunology, 2011, 18(2):280-288.*

International Search Report issued in PCT/KR2020/008364, mailed Mar. 24, 2021.

Abautret-Daly et al. "Harnessing the antibacterial and immunological properties of mucosal-associated invariant t cells in the development of novel oral vaccines against enteric infections," Biochemical Pharmacology 92(2):173-183 (2014).

Dantzler et al., "Emerging role of γδ t cell in vaccine-mediated protection from infectious diseases," Clinical & Translational Immunology 8(8):e1072 (2019). doi: 10.1002/cti2.1072.

Kim et al. "Glycolipid ligands of invariant natural killer t cell as vaccine adjuvants," Expert Reviews Vaccines 7(10):1519-1532 (2008).

Lee et al. "Mincle and sting-stimulating adjuvants elicit robust cellular immunity and drive long-lasting memory responses in a foot-and-mouth disease vaccine," Frontiers in Immunology 10:2509 (2019). doi: 10.3389/fimmu.2019.02509.

Arai et al., (2003) "Effects of intracellular reactive oxygen species generated by 6-formylpterin on T cell functions," Biochem Pharmacol. 67(6):1185-93.

Awad et al., (2018) "Mucosal-associated invariant T cell receptor recognition of small molecules presented by MR1," Immunol Cell Biol. 96(6):588-597.

(Continued)

*Primary Examiner* — Barry A Chestnut

(74) *Attorney, Agent, or Firm* — MEDLER FERRO WOODHOUSE & MILLS PLLC

(57) ABSTRACT

The present inventors have found that innate immune response and T cell exhaustion pathway are more greatly over-expressed in pigs than cattle, such that the pigs are less likely to form adaptive and humoral immune responses than cattle. It would be suggested herein an innovative strategy for improvement of abnormal immune responses in pigs by simultaneously inducing potent cellular and humoral immune responses and applying T cell agonists as a new vaccine adjuvant. This result may provide an important clue for understanding a difference in the immune response between the cattle and pigs, while suggesting a method for maximizing the immune response and vaccine efficacy, which are less expressed in pigs than cattle.

5 Claims, 28 Drawing Sheets

(56) References Cited

OTHER PUBLICATIONS

Cao et al., (2014) "Adjuvants for foot-and-mouth disease virus vaccines: recent progress," Expert Rev. Vaccines 13(11):1377-1385.

Dunne et al., (2010) "(E)-4-Hydroxy-3-methyl-but-2 enyl pyrophosphate-stimulated Yy9Yö2 T cells possess T helper type I-promoting adjuvant activity for human monocyte-derived dendritic cells," Cancer Immunol Immunother. 59:1109-1120.

Dwivedi et al., (2016) "Adjuvant effects of invariant NKT cell ligand potentiates the innate and adaptive immunity to an inactivated H1N1 swine influenza virus vaccine in pigs," Vet Microbiol. 186:157-63.

Ko et al., (2005) "α-Galactosylceramide Can Act As a Nasal Vaccine Adjuvant Inducing Protective Immune Responses against Viral Infection and Tumor," J Immunol. 175(5):3309-3017.

Mori et al., (2000) "Effects of 6-formylpterin, a xanthine oxidase inhibitor and a superoxide scavenger, on production of nitric oxide in RAW 264.7 macrophages," Biochim Biophys Acta. 1474(1):93-9.

Takamatsu et al., (2006) "Porcine γδ T cells: Possible roles on the innate and adaptive immune responses following virus infection," Veterinary Immunol Immunopathol. 112:49-61.

Wen et al., (2012) "Characterization of immune modulating functions of γδ T cell subsets in a gnotobiotic pig model of human rotavirus infection," Comp Immunol Microbiol Infect Dis. 35:289-301.

* cited by examiner

IMMUNE ADJUVANT AND VACCINE COMPOSITION INCLUDING THE SAME

TECHNICAL FIELD

The present invention relates to a novel immune immune-enhancer ("adjuvant"), and specifically to a novel immune adjuvant including unconventional T cell agonists and conventional T cell agonists, and a vaccine composition including the same.

BACKGROUND ART

Foot-and-mouth disease (FMD) is an acute infectious disease that spreads very rapidly in ungulates ("hoofed animals"), and particularly cattle and pigs, causing significant loss in animal productivity and economic aspect. Most clinical studies on FMD have focused on improving vaccine efficacy in cattle rather than pigs. The Office International Epizooties (OW) guidelines for the production of FMD vaccines only define procedures for efficacy testing in cattle, not pigs. However, the severity of FMD is highly dependent on both the viral strain and the affected host species. Acute clinical FMD is more severe in pigs than in other ruminants, and infected pigs may excrete large amounts of aerosol virus, which increases the risk of serious disease spread.

According to recent vaccination trends in Korea, the FMD vaccine effectively induces an immune response in cattle, but in pigs, despite the high virus neutralization antibody titer (Virus Neutralization (VN) Titer), it is not an immune response sufficient for complete protection against FMD virus infection. This difference can be explained by the susceptibility of each animal to the virus or the immune response of the host to vaccination.

Vaccination containing inactivated foot-and-mouth disease virus (FMDV), i.e., an inactivated antigen, is primarily used for host defense and FMD control. In order to improve the immunogenicity and efficacy of the vaccine, an adjuvant such as an oil emulsion (assistant) and an immune enhancing agent such as saponin or gel are added as vaccine components. Recently, a pattern recognition receptor (PRR) ligand including cytokines (e.g., IL-15, IL-18 and IFNα), poly(I:C) as toll-like receptor (TLR)-3 agonists, CpG as TLR-9 agonists and R848 (resquimod) as TLR-7/8 agonists has been proposed as a novel FMD vaccine adjuvant. However, these studies have been conducted at a basic level, and very few mechanisms have been studied to further understand the FMDV antigen or FMD vaccine-mediated cellular and humoral immune responses.

The present invention is intended to develop an adjuvant for immune improvement and a FMD vaccine composition including the same, which use agonists of unconventional T cells including, for example, γδ (gamma delta) T cells, invariant natural killer (iNK) T cells and mucosal-associated invariant T (MAIT) cells, which act as a linker between innate and humoral immune responses, and are proposed as "new protectors" in host defense, as well as conventional T cells such as "T cells" are used as a vaccine adjuvant to directly stimulate T cells without stimulation of antigen presenting cells (APCs) such as dendritic cells (DCs), macrophages (MΦs), monocytes, etc., and thus induce a faster and stronger cellular immune response, such that they play an important role in the initial defense of the host during vaccination, and stimulate cellular and humoral immune responses simultaneously, thereby inducing a strong memory response and high titer antibody in animals, in particular, pigs.

REFERENCES

Non-Patent Document

Lee, M. J. et al. Mincle and STING-stimulating adjuvants elicit robust cellular immunity and drive long-lasting memory responses in a foot-and-mouth disease vaccine. *Front. Immunol.* 10, 2509 (2019).

SUMMARY OF INVENTION

Problems to be Solved by Invention

In order to solve the above problems, an object of the present invention is to provide a novel immune-enhancer ("adjuvant") composition which induces a strong cellular immune response by direct activation of unconventional T cells and conventional T cells in bovine and pig immune cells.

In addition, another object of the present invention is to provide a vaccine composition including the immune adjuvant composition.

Means for Solving Problems

In order to achieve the above objects, the present invention provides a novel immune adjuvant composition which induces a strong cellular immune response in bovine and pig immune cells.

The novel adjuvant includes an unconventional T cell agonist and a conventional T cell agonist as active ingredients.

As used herein, an immunostimulant or adjuvant refers to a substance that enhances an immune response caused by an antigen. The immune adjuvant can exhibit the same efficacy even with a small amount of antigen in the vaccine, such that a vaccine can be made with about one-half to one-third of the conventional antigen.

The conventional T cell agonist in the present invention includes RAR-related orphan receptor gamma t (RORγt).

The unconventional T cell agonist in the present invention means a T cell agonist other than the already known conventional T cell agonists as described above. The unconventional T cell agonist may include a γδ T cell agonist, an iNKT cell agonist, or a MAIT cell agonist, but it is not limited thereto.

The unconventional T cell agonist or conventional T cell agonist may be included in an amount of 0.01 to 1% by weight ("wt. %"), preferably 0.1 to 0.5 wt. %, and more preferably 0.2 to 0.3% wt. % based on a total weight of the immune adjuvant composition. If the content thereof is less than the above range, immune enhancing effects not be expressed. On the other hand, if the content thereof exceeds the above range, toxicity may be induced.

The immune adjuvant or immune adjuvant composition of the present invention may further include oils (or oil emulsions), emulsifiers, gels, and the like, which are well known in the art in addition to the above components.

The oil (or oil emulsion) may include ISA 201, ISA 61, ISA 50, ISA 206, or ISA 207, but it is not limited thereto.

The emulsifiers include substances generally recognized as emulsifiers, such as TWEEN® or other products of the SPAN® product line (fatty acid esters of polyethoxylated sorbitol, and fatty acid-substituted sorbitan surfactants, respectively) and other solubility enhancing agents such as PEG-40 castor oil or other PEGylated hydrogenated oils, but they are not limited thereto.

Further, although the immune enhancing agent (or adjuvant) composition generally has excellent immune enhancing effects in an oil formulation, the immune adjuvant composition according to the present invention shows excellent immune enhancing effects even in a non-oil formulation.

The vaccine composition may further include additives, excipients, carriers, etc. commonly used in the art for preparing the immune adjuvant, and may be prepared by a conventional manufacturing method used for preparing an immune enhancing formulation in the art.

Immune enhancing effects appearing after administration of the immune adjuvant composition of the present invention may be caused by an immune mediator or cells, in particular, may include cellular immunity, mucosal immunity, and humoral immunity enhancing effects, but they not limited thereto.

The immunity may include immunity against infection or cancer against any one of viruses, fungi, bacteria and parasites, but it is not limited thereto.

The virus may include foot-and-mouth disease virus (FMDV), *Leishmania*, Human Immunodeficiency virus (HIV), Hepatitis C virus (HCV), Hepatitis E virus (HEV), Hepatitis A virus (HAV), Hepatitis B virus (HBV), tuberculosis, Herpes Simplex virus (HSV), malaria causing parasites, human papilloma virus (HPV), influenza virus, measles virus, mumps virus, Ebola virus, respiratory syncytial virus (RSV), West Nile virus (WNV), and the like, but it is not limited thereto.

In addition, the present invention provides a vaccine composition including the adjuvant composition.

The immune adjuvant composition may be included in an amount of 30 to 70 wt. %, and preferably 40 to 50 wt. % based on the total weight of the vaccine composition, but it is not limited thereto. If the amount thereof is less than the above range, effects of the vaccine may not be expressed. On the other hand, if the amount thereof exceeds the above range, toxicity may be induced during administration.

The vaccine composition may further include additives, excipients, carriers, etc. commonly used in the art to prepare a vaccine composition.

Further, the vaccine composition may be prepared by a conventional manufacturing method used in the art to prepare a vaccine composition.

In the present invention, the type of the vaccine is not limited, but preferably a virus vaccine, and more preferably a foot-and-mouth disease vaccine.

When the foot-and-mouth disease vaccine composition contains the immune adjuvant according to the present invention, the foot-and-mouth disease vaccine composition may express immune effects against foot-and-mouth disease virus 0 serotype, A serotype, Asia serotype, C serotype, SAT1 serotype, SAT2 serotype, SAT3 serotype, etc. Preferably the immune effects may be more potent against foot-and-mouth disease virus 0 serotype and A serotype.

The vaccine composition may be administered by any of sublingual, transdermal, rectal, transmucosal, topical, oral, intrapleural, intravenous, intraarterial, intraperitoneal, subcutaneous, intramuscular, intranasal, intrathecal and intra-articular administration and the like.

Advantageous Effects

The present invention may provide a novel immune adjuvant capable of enhancing the humoral immune response more efficiently by reinforcing the innate cellular immune response of cattle and pigs, as well as a vaccine composition including the same.

MODE FOR CARRYING OUT INVENTION

Figure 1:
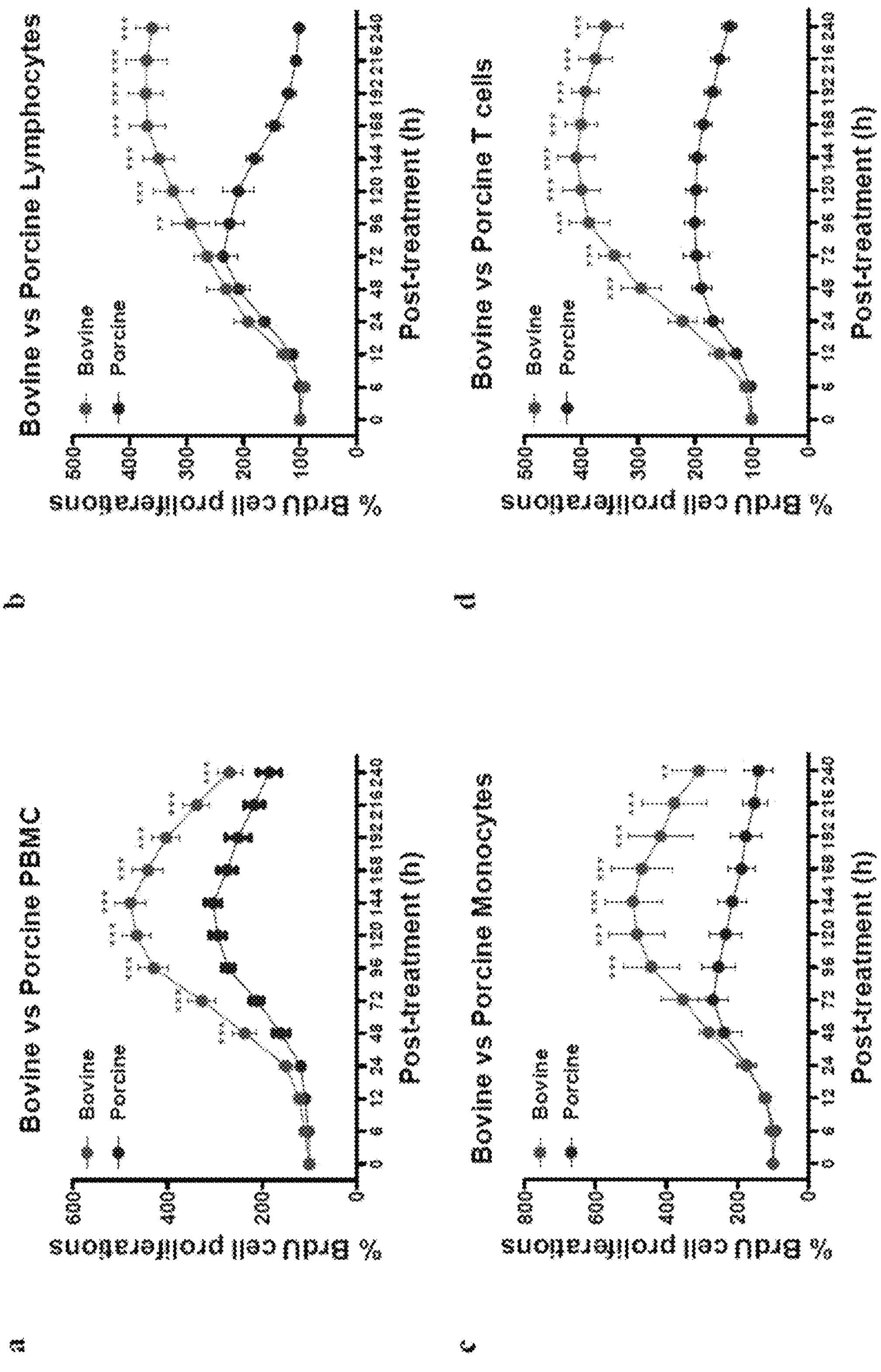
FIG. 1 shows results of proliferation of PBMCs, lymphocytes, monocytes and T cells in cattle and pigs induced with inactivated FMDV O/TWN/97 antigen.

Hereinafter, the present invention will be described in detail by way of examples and experimental examples.

However, the following examples and experimental examples are merely illustrative of the present invention, and the content of the present invention is not limited to the following examples and experimental examples.

Experimental Materials and Methods

1. Antigen Purification and Inactivation

Purified inactivated viral antigens were prepared in BHK-21 cells infected with FMDV O/TWN/97-R (GenBank AY593823; P1) constructed for phenotypic replacement of P1 by reverse genetics (reference sequence).

For viral infection, the culture medium was replaced with serum-free Dulbecco's Modified Eagle's Medium (DMEM; HyClone, Logan, UT, USA) and cells were inoculated with the virus by incubating at 37° C., 5% carbon dioxide for 1 hour. The extracellular virus was then removed. At 24 h post infection, the virus was inactivated by treatment with 0.003N binary ethylenimine twice for 24 hours in a shaking incubator, followed by concentration with polyethylene glycol (PEG) 6000 (Sigma-Aldrich, St. Louis, MO, USA). The obtained virus concentrate was layered with a 15-45% sucrose density gradient and centrifuged.

After ultracentrifugation, the bottom of the centrifuge tube was punctured and 1 mL fractions were collected. The presence of FMDV particles in the samples of each fraction was confirmed by optical density using a lateral flow device, UA-6 (BioSign FMDV Ag; Princeton BioMeditech, Princeton, NJ, USA). Prior to use in field experiments, the PEG-pretreated supernatant was passed through ZZ-R127 and BHK-21 cells at least twice thus to confirm no occurrence of cytopathic effect (CPE), and thereby demonstrating the absence of live virus in the supernatant.

2. Isolation of PBMCs

To investigate the antigen-mediated immune response, whole blood of pigs and cattle was donated from the Gyeonggi-do Animal Sanitation Laboratory. Whole blood (15 mL) was collected in BD Vacutainer heparin tubes (BD Biosciences, Becton, Dickinson and Company, Franklin Lakes, NJ, USA), followed by Ficoll-Paque™ PLUS gradient (GE Healthcare Bio-Sciences Corp., Piscataway, NJ, USA) and centrifugation. Then, the residual red blood cells were lysed by treatment with ammonium-chloride-potassium (ACK) lysis buffer (Gibco, Carlsbad, CA, USA). PBMCs were suspended in Dulbecco's PBS not containing $Ca^{2+}$ and $Mg^{2+}$ (Gibco), which is supplemented with 2% fetal bovine serum (FBS) (Gibco), followed by counting the same using a volume flow cytometer (MACSQuant Analyzer, Miltenyi Biotec), Bergisch Gladbach, Germany). All cells were freshly isolated immediately before use, and cryopreserved cells were not used in any experiment. Purified PBMCs were re-suspended in RPMI 1640 (Gibco) medium supplemented with 10% FBS (HyClone, Logan, Utah, USA), 3 mM L-glutamine (Sigma-Aldrich) and 100 U/mL penicillin-streptomycin (Sigma-Aldrich). Then, the purified PBMCs were seeded in 25 $cm^2$ tissue culture flasks (Eppendorf, Germany, Hamburg) and incubated at 37° C. with 5% $CO_2$ thus to allow newly isolated monocytes to be adhered thereto. After 3 hours of incubation, non-adherent cells were collected for lymphocyte isolation. The remaining adherent cells were washed extensively with Dulbecco's phosphate buffered saline (DPBS) (Gibco) before adding 4 mL of RPMI 1640 growth medium to each flask, followed by culturing in a 5% $CO_2$ incubator at 37° C.

3. Cell Isolation by Magnetic Activated Cell Sorting (MACS)

Monocytes, lymphocytes and T cells were isolated from PBMCs. For isolation of primary immune cells, monocytes from adherent PBMCs and T cells from non-adherent cells were purified through the MACS. Adherent and non-adherent cells from PBMCs were briefly re-suspended in MACS buffer (1×PBS supplemented with 0.5% BSA and 2 mM EDTA). Monocytes and T cells were sorted using magnetic microbeads along with a monocyte isolation kit and a Pan T cell isolation kit (Miltenyi Biotec), respectively, according to the manufacturer's instructions, and were subjected to further classification using a fluorescence-activated cell sorter (FACS, MoFlo® Astrios™ Cell Sorter, Beckman Coulter, Brea, CA, USA). Purification of the isolated cells was confirmed by flow cytometry (MACSQuant Analyzer, Miltenyi Biotec) and analyzed with FlowJo software version vX.0.7 (TreeStar Inc., Ashland, OR, USA). The purity of the sorted cells was higher than 95%.

4. Generation of Mo-DCs and Mo-MΦs

For the differentiation of Mo-DCs, isolated monocytes were cultured in a complete RPMI 1640 medium (Gibco) supplemented with 10% FBS (HyClone), 3 mM L-glutamine (Sigma-Aldrich), 100 U/mL penicillin-streptomycin (Sigma-Aldrich), 50 ng/mL GM-CSF and IL-4 (Miltenyi Biotec) to generate immature DCs for 7 days. On day 3, an equal volume of the above-mentioned medium was added, and on day 7, non-adherent contaminating cells were removed by vigorous washing before cell lysis. For the isolation of pure DCs, anti-CD11c magnetic beads were used according to the manufacturer's instructions (Miltenyi Biotec). The purity of $CD11c^+$/MHC $II^+$ cells was greater than 95%, and the cells were maintained in a 5% $CO_2$ incubator at 37° C.

For the differentiation of Mo-MΦs, isolated monocytes were seeded in 12-well plates with cells $10^6$/mL and cultured in RPMI 1640 medium (Gibco) supplemented with 10% FBS (HyClone), 1×MEM non-essential amino acids, 1 mM sodium pyruvate, 0.05 mM 2-mercaptoethanol (Sigma-Aldrich), 100 U/mL penicillin-streptomycin (Sigma-Aldrich) and 50 ng/mL macrophage colony stimulating factor (M-CSF) (Abcam, Cambridge, MA, USA) for 6 days. Additional M-CSF was added on day 2 and the whole medium was freshly replaced on day 4. The purity of $CD11b^+$/$F4/80^+$ cells was greater than 95%. Cells were maintained in a 5% $CO_2$ incubator at 37° C.

5. Preparation of Mature DCs

Mature DCs were generated by adding one of the following six treatments: no treatment (no stimulation), LPS (*E. coli* 055:B5, Sigma-Aldrich [100 ng/mL])+rpIFN-γ (Novus Biologicals, LLC., Littleton, CO, USA [20 ng/mL]), rpTNFα (R&D Systems, Minneapolis, Minnesota, USA [20 ng/mL]), antigen alone (antigen [1 μg/mL]), LPS+rpIFNγ+antigen (LPS [100 ng/mL], rpIFN-γ [20 ng/mL] and antigen [1 μg/mL]) or rpTNFα+antigen (rpTNFα [20 ng/mL] and antigen [1 μg/mL]). At specific time points after treatment (0, 6, 12, 24, 48, 72 and 96 h), cell culture supernatants were harvested for ELISA.

6. M1/M2 MΦ's Polarization

After 7 days of growth, Mo-MΦs were treated with one of the following six treatments: no treatment (no stimulation), M1 MΦs (LPS [100 ng/mL] and rpIFN-γ [20 ng/mL]), M2 MΦs. (rpIL-4, R&D Systems [20 ng/mL]), antigen alone (1 μg/mL), M1 MΦ's+antigen (IFN-γ [20 ng/mL] and LPS [100 ng/mL] and antigen [1 μg/mL]) or M2 MΦs+antigen (IL-4 [20 ng/mL]+antigen [1 μg/mL]). At specific time points after treatment (0, 6, 12, 24, 48, 72 and 96 h), cell culture supernatants were harvested for ELISA.

7. Cell Culture, Antigen Treatment and BrdU Integration Assay in Bovine and Porcine PBMCs Isolated or differentiated cells (1×$10^6$ cells/well) were cultured with a complete medium consisting of 10% fetal calf serum (HyClone), 3 mM L-glutamine (Sigma-Aldrich), 10 mM HEPES, 100 U/mL penicillin-streptomycin (Sigma-Aldrich) and RPMI 1640 medium (Gibco) supplemented with 0.05 mM 2-mercapto ethanol (Sigma-Aldrich) in a 5% $CO_2$ incubator at 37° C. (Sigma-Aldrich). For stimulation, the cells were treated with 1 μg of each antigen. At specific time points after treatment (0, 6, 12, 24, 48, 72, 96, 120, 144, 168, 192, 216 and 240 h), the BrdU cell proliferation assay kit (cells Signaling Technology, MA, USA) based on the incorporation of BrdU was used to test cell proliferation according to the manufacturer's instructions during DNA synthesis. Briefly, 10 μM BrdU was added to the cell culture, followed by culturing at 37° C. for 4 h. Cells were then fixed and incubated with anti-BrdU mouse monoclonal antibody, followed by applying horseradish peroxidase-conjugated goat anti-mouse antibody. Tetramethyl benzidine as a color development substrate was used for color development. Absorbance was measured at a dual wavelength of 450/550 nm. Cell viability was monitored using the Cell Titer-Blue™ assay kit (Promega, Madison, WI, USA). Compared to the medium-only control treatment, the experimental treatment did not affect cell viability.

8. ELISA

ELISA for bovine and porcine IL-1β, IL-6, IL-10, IL-12/23p40, IL-23 and TNFα (DuoSet, R&D Systems, Minneapolis, MN, USA; Cloud-Clone Corporation, Houston, USA) was performed using the cell culture supernatant according to the manufacturer's instructions.

9. Inhibition of Phagocytosis

To inhibit phagocytosis, Mo-DCs and Mo-MΦs were incubated with 5 μg/mL cytochalasin D (CytD) (Sigma-Aldrich) for 45 min before antigen treatment. Then, CytD-treated Mo-DCs and Mo-MΦs were cultured with 1 μg/mL antigen. After 6 hours, the cultured supernatant was collected for ELISA.

10. Cattle and Pigs

To understand a fundamental difference in the immune response between the cattle and pigs in natural condition and FMDV O antigen-mediated immune response and associated mechanism, field experiments using cattle and pigs were performed according to the method described in Lee et al. FMD antibody-negative animals were used (cattle: 5 months old, pigs: 10-12 weeks old). The cattle and pigs were divided into two groups (n=5/group). Animals were kept in isolation during the study. The study was conducted in accordance with institutional guidelines with the approval of the Animal Experimental Ethics Committee (approval numbers IACUC-2018-800 and IACUC-2019-185) of the Agriculture, Forestry and Livestock Quarantine Headquarters.

11. Vaccination and Sampling

O/TWN/97-R Ag was used as the FMD antigen, and the vaccine composition for the positive control was as follows: 1 mL of vaccine prepared in a single dose containing 15 μg of O/TNW/97-R antigen (one dose for bovine and swine use), ISA 206 (50%, w/w), 10% $Al(OH)_3$ and 150 μg Quil-A. For isolation of naive PBMCs, whole blood was collected from cattle and pigs of naive controls (foot-and-mouth disease antibody-negative). Vaccinations were performed twice at a 28-day interval, and 1 mL vaccine (one dose) was injected into the neck of the positive control animals via the deep intramuscular route. Blood samples were collected from the cattle and pigs at 0, 14, 28, 42, 56, 70 and 84 dpv for serological analysis, and further at 28 dpv (28 days after $1^{st}$ inoculation dose, before $2^{nd}$ inoculation dose) for PBMCs isolation from the cattle and pigs. Animals were monitored daily for body temperature, symptoms at the site of vaccination and appetite. Serum samples were stored at −80° C. until test was performed.

12. RNA Sequence Analysis (RNA-Seq)

For RNA-Seq analysis, PBMCs from whole blood of cattle and pigs in the naive control (n=3/group) and in the positive control (n=3/group) (28 dpv) were subjected to density gradient centrifugation using Ficoll-Paque™ PLUS according to the method described by Lee, M. J. et al. Mincle and STING-Stimulating Adjuvants Elicit Robust cellular Immunity and Drive Long-Lasting Memory Responses in a Foot-and-Mouth Disease Vaccine. *Front Immunol,* 2509 (2019) (hereafter, Lee et al.) (GE Healthcare Bio-Sciences Corp., Piscataway, NJ, USA).

13. Library Construction and Sequencing

Illumina-based next generation sequencing (NGS) was implemented to obtain high-throughput bovine and porcine transcriptome data. Total RNA was individually extracted from bovine and porcine PBMCs using TRIzol Reagent (Invitrogen) and RNeasy Mini Kit (QIAGEN) according to the manufacturer's protocol. The total RNA was then quantified using a Nanodrop spectrophotometer (Thermo Scientific, Wilmington, USA), and its quality was assessed by RNA 6000 Nano Assay Kit (Agilent Technologies, Santa Clara, USA) and Bioanalyzer 2100 (Agilent). NGS sequencing libraries were generated from 1 of total RNA using the TruSeq RNA Sample Preparation Kit (Illumina, San Diego, CA, USA) according to the manufacturer's protocol. That is, poly-A-containing RNA molecules were purified using poly-T oligo-attached magnetic beads. After purification, total poly(A)+RNA was fragmented into small pieces using divalent cations at a high temperature. The cleaved mRNA fragments were subjected to reverse transcription into first-strand cDNA using random primers. Short fragments were purified with QiaQuick PCR extraction kit and digested with elution buffer for final recovery and addition of poly(A). The short fragment was then ligated with a sequencing adapter. Each library was separated by adjoining different MID tags. The resulting cDNA library was then subjected to paired-end sequencing (2×101 bp) to the samples by a NovaSeg™ 6000 system (Illumina).

14. Gene Expression Analysis

Low-quality bases (PHERD score (Q)<20) and adapter contamination were removed using ILLUMINACLIP: TruSeq3-SE:2:30:10 LEADING:3 SLIDINGWINDOW:4: 15 MINLEN:36' as a default parameter by Trimmomatic v. 0.36. After quality score verification and read length verification, RNA-Seq read values were mapped in the reference Bostaurus genome (published on April 2018; ARS-UCD1.2; GCA 002263795.2) using STAR as a basic default parameter and the expected maximization (RSEM, RNA-Seq). In order to obtain an expression value for each gene/transcriptome in the genome, the expression was estimated by Expectation-Maximization method. Reading counts estimated by RSEM were applied to edgeR v3.22.5 so as to obtain differential expression scores with statistical significance. Further, filters, i.e. transcripts per million (TPM)≥0.3, read counts ≥5 and $\log_2$ fold change ≥1 were applied to the selection of differentially expressed transcriptomes. Finally, expressed transcripts (i.e., TPM≥0.3 and read count≥5) were analyzed to reveal an expression pattern in each condition and gene family (immune genes, T cell markers and TLR, CDS, CLR signaling pathway genes).

15. Ingenuity Pathway Analysis (IPA)

Then, expression profiles were grouped into clusters of similar expression patterns. The rich pathways, networks and functions were then analyzed using IPA (QIAGEN Inc., qiagenbioinformatics.com/products/ingenuity-pathway-analysis). Finally, an in-house R script was used to create a binary heat map showing all genes involved in critical pathways.

<Evaluation and Experimental Method of Effect of Unconventional T Cell Agonists as Potent Vaccine Adjuvant>

1. Mouse

Age- and sex-matched wild-type C57BL/6 mice (6-7 week old females) were purchased from KOSA BIO Inc. (Gyeonggi-do). All mice were placed in micro-separation cages in a specific pathogen free (SPF) animal facility at Animal Biosafety Level 3 (ABSL3) in the Agriculture, Forestry and Livestock Quarantine Headquarters. The study was conducted with the approval of the Animal Experimental Ethics Committee (Approval Nos. IACUC-2018-800 and IACUC-2019-185) of the Agriculture, Forestry and Livestock Quarantine Headquarters in accordance with institutional guidelines.

2. Unconventional T Cell Agonist and Conventional T Cell Agonist-Mediated Adjuvant and Host Defense Responses and the potential of unconventional and conventional T cell agonists as FMD vaccine adjuvant, and in order to investigate their protective effects against FMDV infection, experiments were performed using the presented strategy (FIG. 7A) (n=10 per group). The O/TWN/97-R antigen was used as the inactivated FMDV antigen. The vaccine composition for PC group is as follows: O/TWN/97-R antigen (15 μg/dose/mL, 1/10 dose for bovine and swine use), 10% $Al(OH)_3$ and 15 μg/Quil-A/mouse were used, therefore, the total volume is 100 μL. To all mice in the experimental group, an unconventional T cell agonist or a conventional T cell agonist as an adjuvant (immune adjuvant) was added to reach about 0.2 wt. % based on the total weight of the adjuvant composition, and thus to reach about 0.1 wt. % based on the total weight of vaccine, such that a vaccine was provided with the same composition as a PC group.

Unconventional T cell agonists and conventional T cell agonists used in these experiments were purchased as follows: Sigma-Aldrich (γδ T cell agonist; Isopentenyl pyrophosphate trilithium salt, IPP (I),(E)-1-hydroxy-2-methyl-2-butenyl 4-pyrophosphate lithium salt, HMP (H), Abcam (iNKT cell agonist; α-galactosyl ceramide; α-galcer (G), T cell agonist (RORγT (R)) and Cayman (MAIT cell agonist; 6-formylpterin (F)) and Cayman Chemical, Ann Arbor, MI, USA).

Mice in the negative control received the same volume of phosphate buffered saline (PBS, pH 7.0) via the same route. Briefly, vaccinations were performed twice at a 35-day interval, and mice were vaccinated intramuscularly in the thigh muscles. Later, at either 84 dpv or 168 dpv, mice were challenged with FMDV (100 LD50 of O/VET/2013, ME-SA topotype) by intraperitoneal injection. The viability and body weight of mice were monitored up to 7 dpc (7 days post challenge, 7 days after challenge inoculation). Further, sera sampled from mice at 0, 7, 14, 28, 56, 84 and 168 dpv were subjected to analysis through a type A structural protein enzyme-link immune adsorption analysis (structural protein (SP) A ELISA) and virus neutralization (VN) titer, so as to examine the induced cellular and humoral immune responses.

3. Serological Analysis

For detection of SP antibodies in serum, the PrioCHECK FMDV type 0 ELISA kit (Prionics AG, Switzerland) was used as described in Lee et al. Absorbance in an ELISA plate was converted to percent inhibition (PI) values. When the PI value was 50% or higher, the animal was considered antibody positive.

VN test was performed according to the manual of the World Organization for Animal Health (OIE) as described in Lee et al. Serum was inactivated through heat treatment in a water bath at 56° C. for 30 minutes. Cell density was adjusted to form a 70% monolayer, and 2-fold serial dilutions (1:8 to 1:1024) of the serum samples were prepared. The diluted serum samples were then incubated with 100-tissue culture infectious dose $(TCID)_{50}$/0.5 mL homologous virus at 37° C. for 1 hour. After 1 hour, LF-BK (bovine kidney) cell suspension was added to all wells. After 2-3 days, the CPE was checked to determine the titer, which was calculated as $Log_{10}$ of the reciprocal antibody dilution required to neutralize 100 $TCID_{50}$ of the virus.

4. PBMCs Isolation

FMD antibody negative animals were used as donors (n=3/group) for isolation of porcine PBMCs. Whole blood (15 mL/each donor) was independently collected in BD Vacutainer heparin tubes. The detailed protocol for PBMCs isolation was mentioned above. All cells were freshly isolated immediately before use, and cryopreserved cells were not used in any experiments. The purified PBMCs were then re-suspended in RPMI 1640 medium (Gibco, Carlsbad, CA, USA) supplemented with 10% FBS (HyClone), 3 mM L-glutamine (Sigma-Aldrich) and 100 U/mL penicillin streptomycin (Sigma-Aldrich). The product was plated at $1\times10^5$ cells per well in 96-well plates and incubated at 37° C. with 5% $CO_2$. After 3 hours of incubation, the culture medium was replaced with a serum-free medium prior to stimulation with either of FMDV O (O/TWN/97-R) antigen alone or in combination with various unconventional T cell agonists and T cell agonists or PRR ligands.

5. BrdU Integration Assay in Porcine PBMCs

A detailed protocol for the cell proliferation assay is mentioned above. At 12 and 36 hours after treatment with unconventional T cell agonists and conventional T cell agonists, cell proliferation was tested according to the manufacturer's instructions.

6. RNA-Seq

For RNA-Seq analysis, porcine PBMCs were isolated from whole blood (n=3/group) of FMD antibody-negative pigs in serum. The isolated PBMCs were treated with: unconventional T cell agonists including γδ T cell agonist (isopentyl pyrophosphate trilithium salt, IPP (I)), (E)-1-hydroxy-2-methyl-2-butenyl 4-pyrophosphate lithium salt, HMP (H)), iNKT cell agonists (α-galactosyl ceramide, α-Galcer (G), Abcam) and MAIT cell agonists (6-formylprine, 6-Formylpterin (F), Cayman Chemical); T cell agonists (RORγT (R), Abcam), PRR ligands (Resiquimod, R848, TLR-7/8 agonist) and trehalose-6, 6-divehenate (TDB, Mincle agonist); TDB and bis-(3'-5)-cyclic dimer guanosine monophosphate (c-di-GMP, STING agonist, InvivoGen, San Diego, CA, USA) in combination with FMDV O (O/TWN/97-R). Then, after 12 hours of incubation, PBMCs were collected (preparation), and RNA was extracted for qRT-PCR.

Library construction and sequencing, gene expression analysis and IPA were performed as described above.

7. Statistical Assay

All quantitative data are expressed as mean±SEM unless otherwise mentioned. Comparison of values for statistical significance between groups was performed using one-way ANOVA with Tukey's multiple comparison test or Student's t-test in order to compare two data points. For statistical assay, GraphPad Prism 8.3.1 software (GraphPad Software, San Diego, USA) was used.

<Preliminary Experimental Example. Assessment of Differences in Immunity Between Cattle and Pigs>

1. FMDV antigen induces more strong proliferation in bovine PBMCs, lymphocytes, monocytes and T cells than those derived from pigs.

O/TWN/97-R antigen-mediated proliferation of bovine and porcine PBMCs, lymphocytes, monocytes and T cells was observed using the BrdU cell proliferation assay. Proliferation of all bovine cell types was significantly higher than that of pig cells ($p<0.001$) (a to din FIG. 1).

2. FMDV antigen significantly induces pro-inflammatory cytokine expression in bovine immune cells compared to porcine immune cells.

Figure 2A:
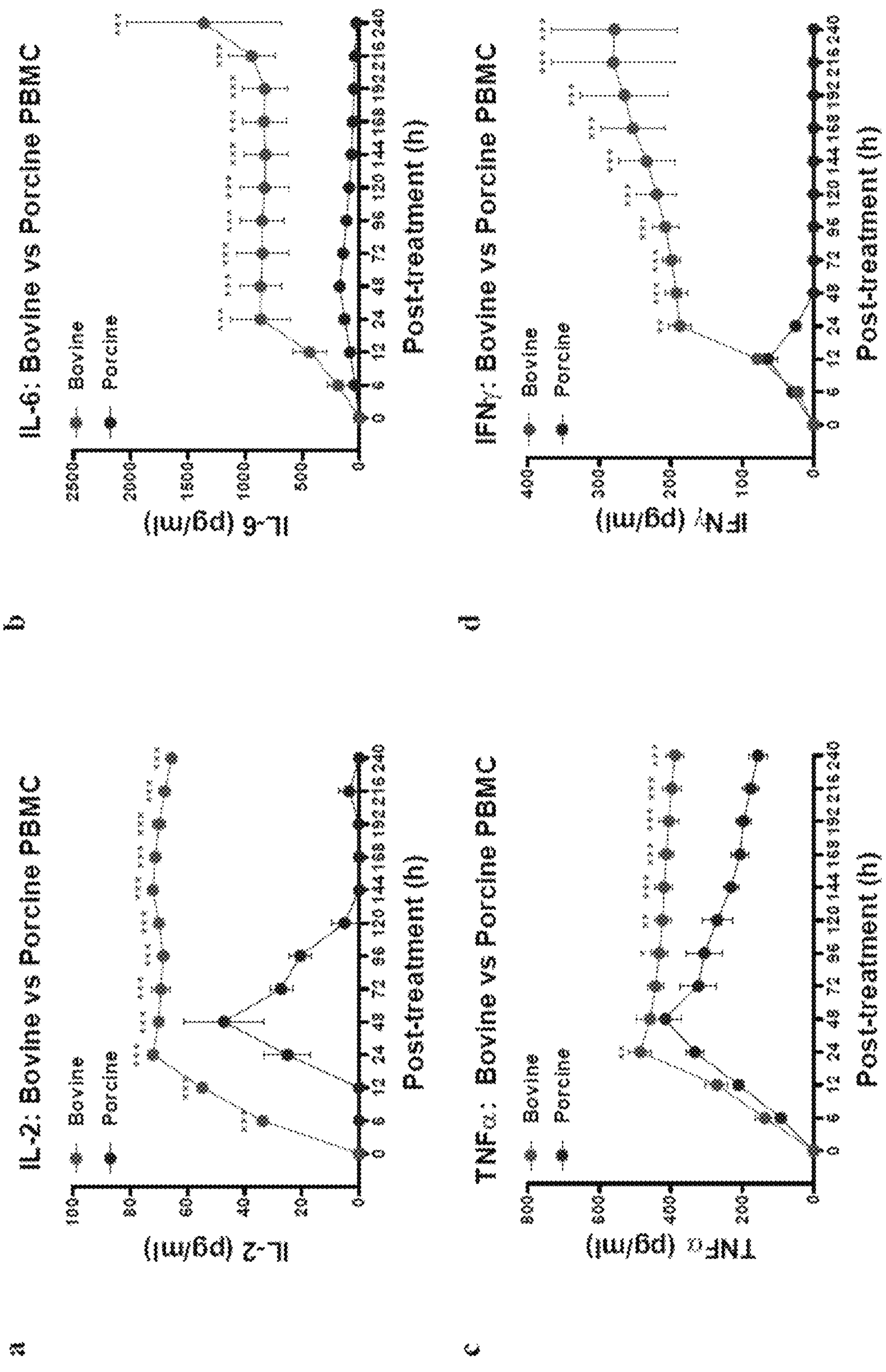
FIGS. 2A to 2D, and FIG. 3 show results of pro-inflammatory cytokine expression in porcine immune cells and bovine immune cells mediated by FMDV (O/TWN/97-R) antigen.

O/TWN/97-R antigen-mediated cytokine expression assay showed that cytokine expression in porcine PBMCs peaked at 12 to 48 h and then decreased sharply, whereas the cytokine expression was shown to be increased markedly within 24 hours in bovine PBMCs and this level was maintained up to 240 hours (a to d in FIG. 2A, Table 1).

Figure 2B:
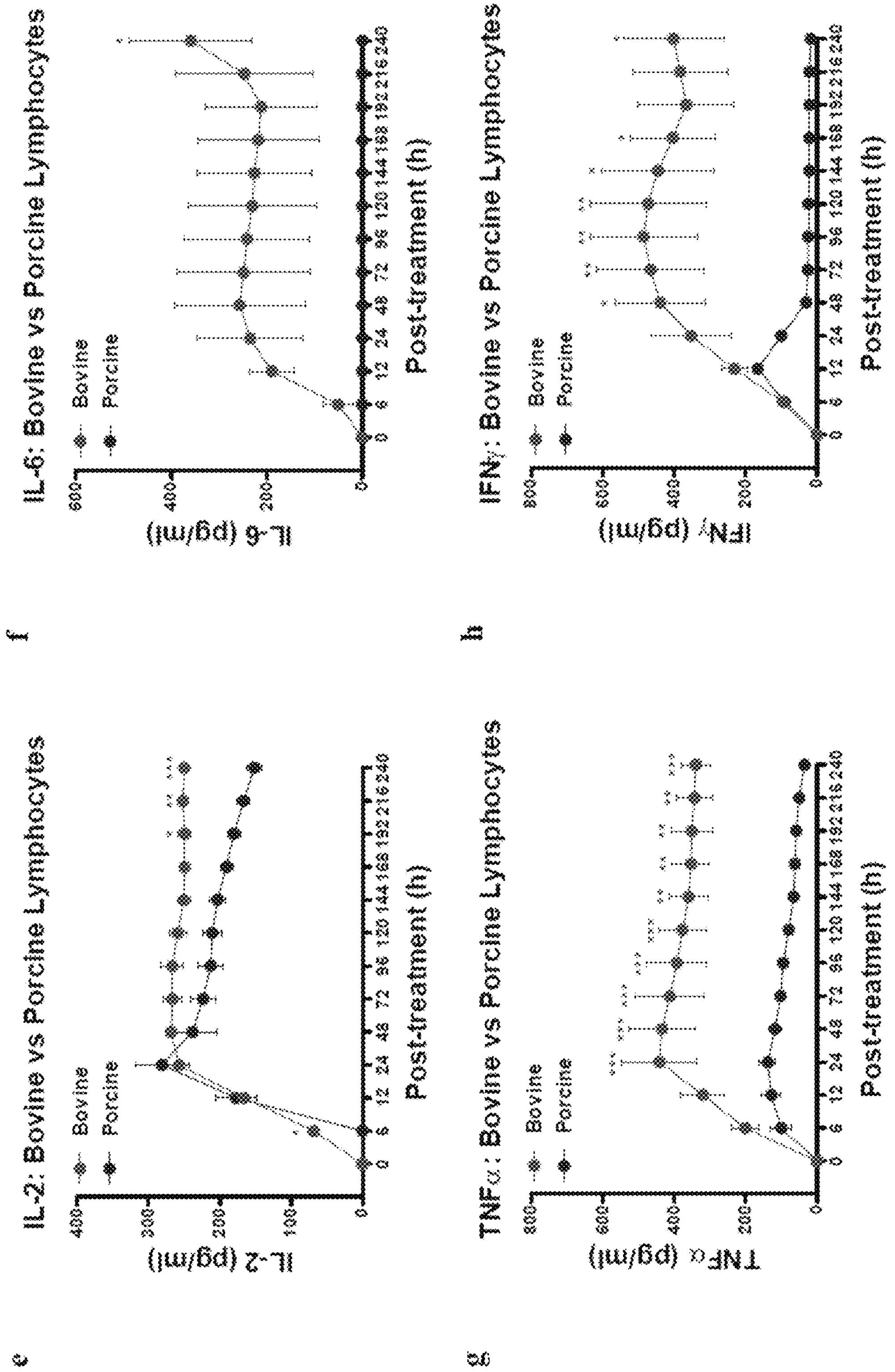
Figure 2C:
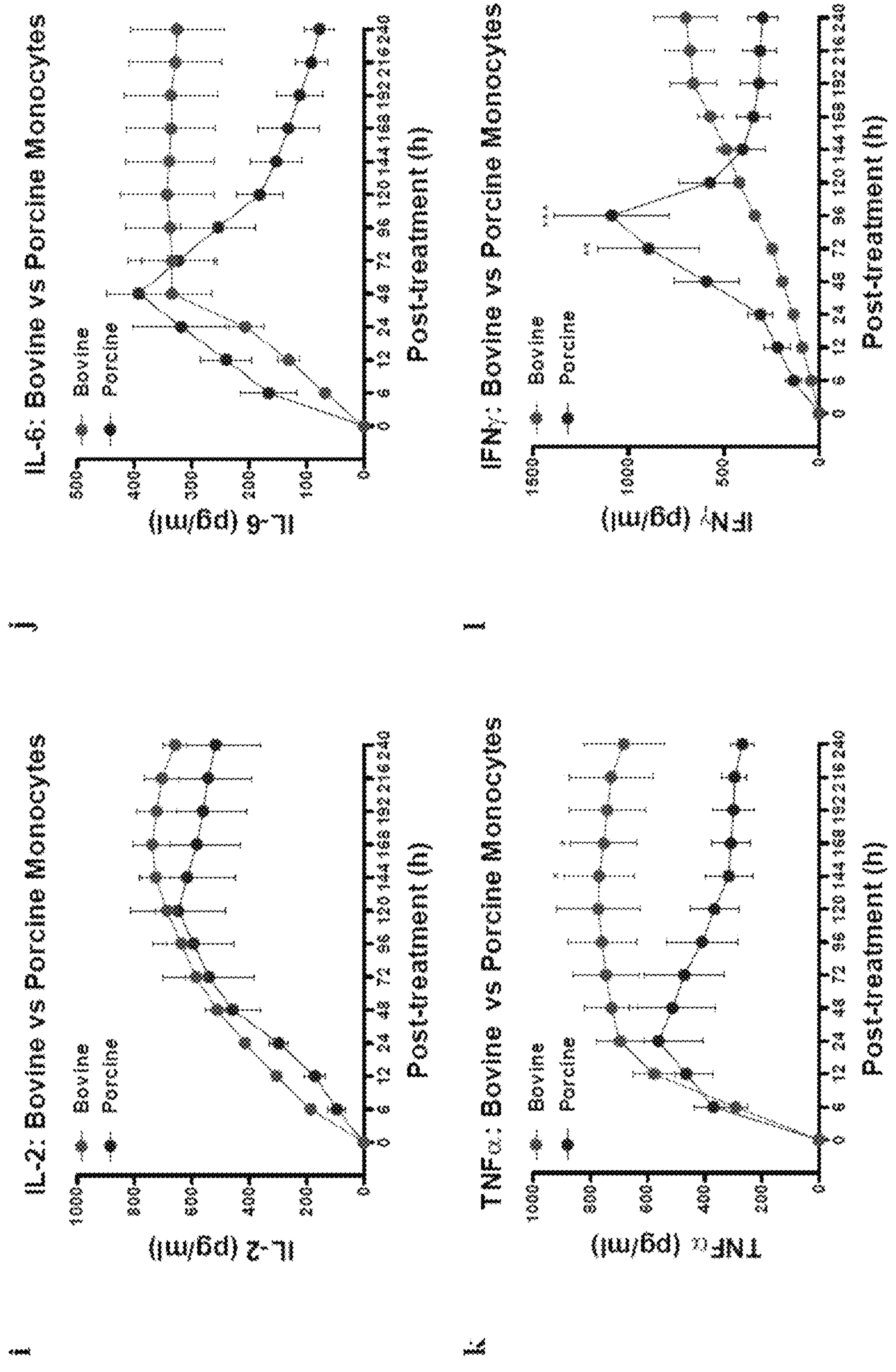
Figure 2D:
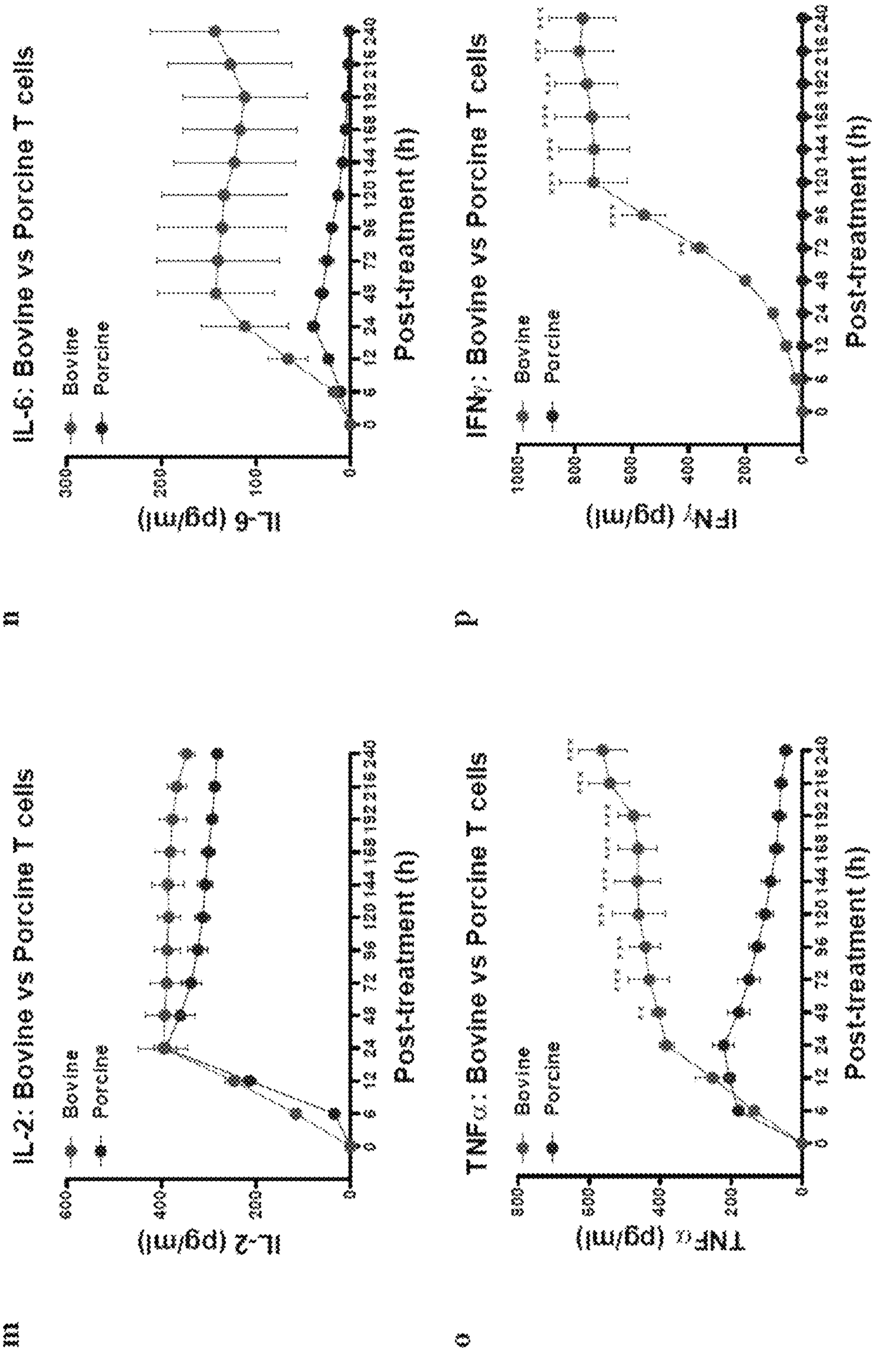

In lymphocytes, O/TWN/97-R antigen-mediated cytokine expression was significantly higher in bovine cells than in porcine cells (e to h in FIG. 2B, Table 1). Regarding the expression of O/TWN/97-R antigen-mediated cytokines in porcine monocytes (i to 1 in FIG. 2C, Table 1), IL-2, IL-6, TNFα and IFNγ were further significantly higher in bovine monocytes. The temporal changes in O/TWN/97-R antigen-mediated cytokine expression in bovine and porcine T cells were evaluated (m to p in FIG. 2D, Table 1). Cytokine expression was increased rapidly in both T cell types up to 24 hours, then gradually decreased in porcine T cells but remained almost constant in bovine cells until 240 hours.

Figure 3:
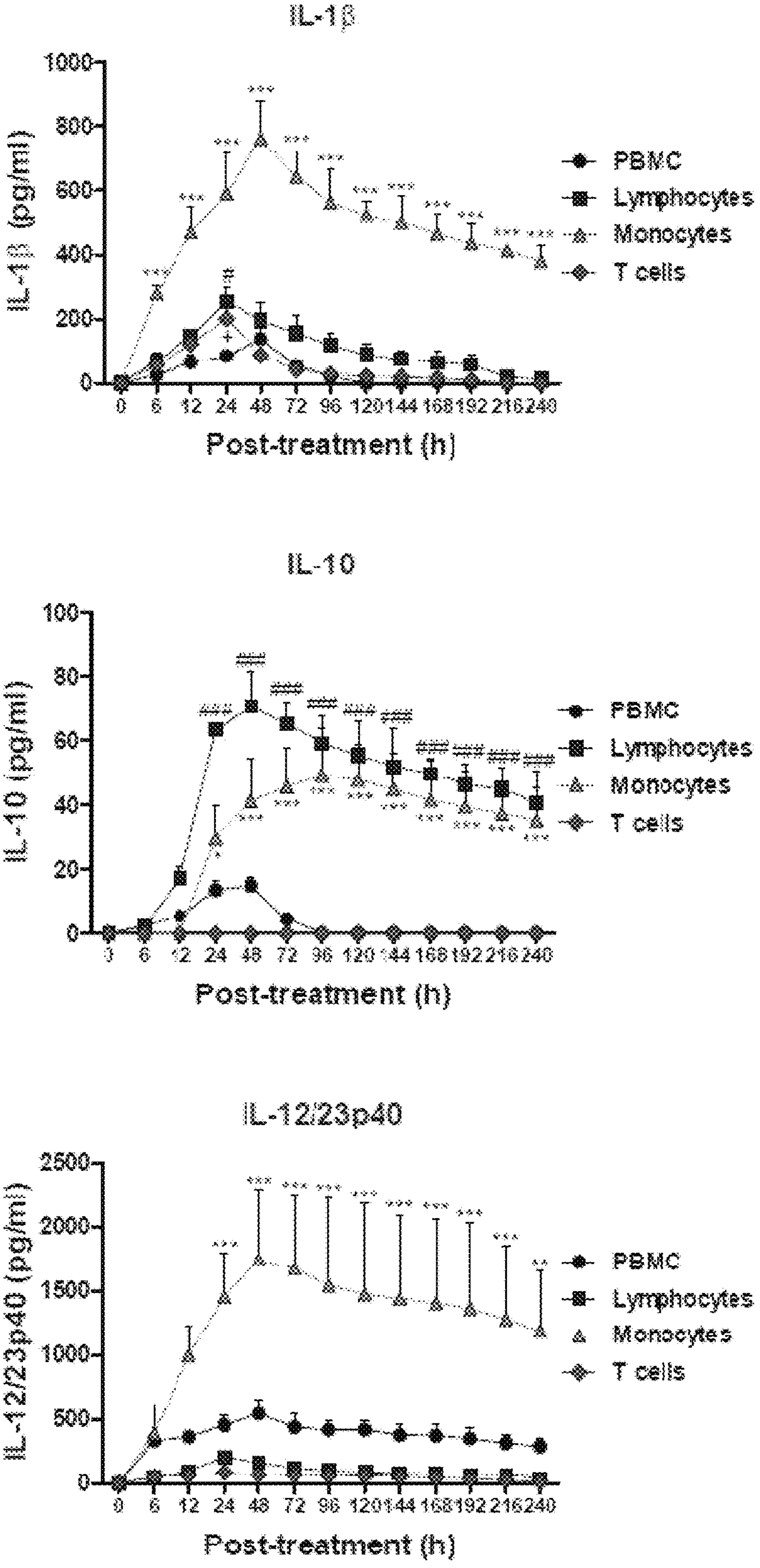

The kinetics of IL-10, IL-12/23p40 and IL-10 expression were identified in porcine PBMCs, lymphocytes, monocytes and T cells. The expression of IL-10 and IL-12/23p40 as pro-inflammatory cytokines was high, and the expression of the anti-inflammatory cytokine IL-10 was remarkably low (FIG. 3).

TABLE 1

| | IL-2 | | IL-6 | | TNFα | | IFNγs | |
|---|---|---|---|---|---|---|---|---|
| Cell | Cow | Pig | Cow | Pig | Cow | Pig | Cow | Pig |
| PBMCs | 70.14 ± 0.69*** | 47.33 ± 13.88 | 858.65 ± 104.74*** | 171.00 ± 23.09 | 458.00 ± 37.91 | 416.43 ± 13.8$^{ns}$ | 192.33 ± 16.22 | ND |
| Lymphocytes | 268.41 ± 4.00 | 238.30 ± 34.21$^{ns}$ | 256.88 ± 137.25 | ND | 434.19 ± 91.92*** | 117.71 ± 16.63 | 439.00 ± 125.37* | 30.22 ± 10.85 |
| Monocyte | 511.06 ± 25.59 | 457.70 ± 93.99$^{ns}$ | 335.27 ± 68.87 | 392.97 ± 54.79$^{ns}$ | 726.86 ± 93.54 | 512.67 ± 150.49$^{ns}$ | 194.33 ± 7.06 | 591.80 ± 171.45$^{ns}$ |
| T cell | 393.36 ± 39.78 | 360.10 ± 31.02$^{ns}$ | 142.35 ± 62.07 | 30.15 ± 6.46 | 404.95 ± 20.14** | 179.00 ± 31.05 | 201.00 ± 15.88 | ND |

Figure 4A:
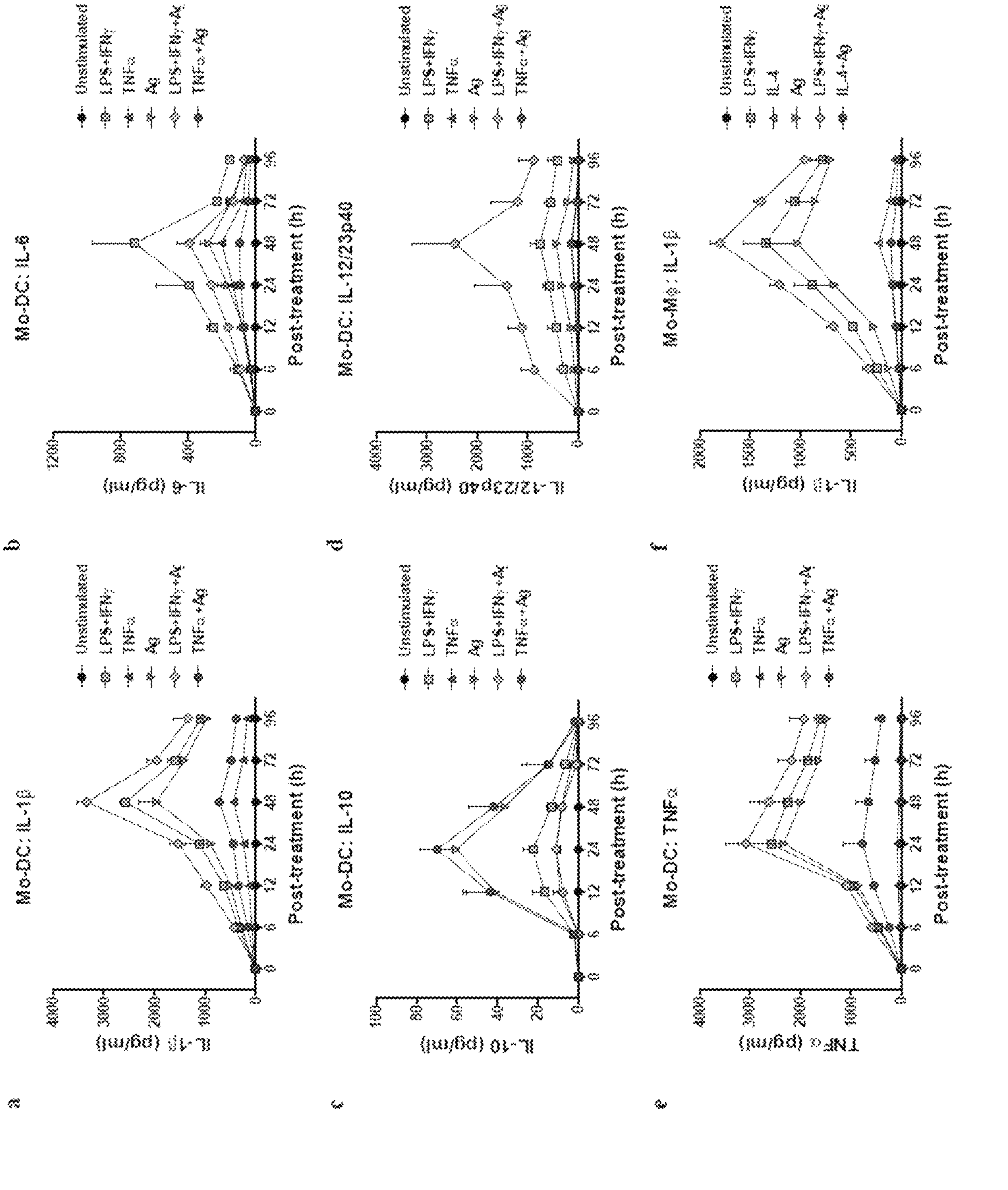
FIGS. 4A and 4B illustrate that FMDV antigen directly stimulates cytokine expression in Mo-DCs and Mo-MΦs of pigs.
Figure 4B:
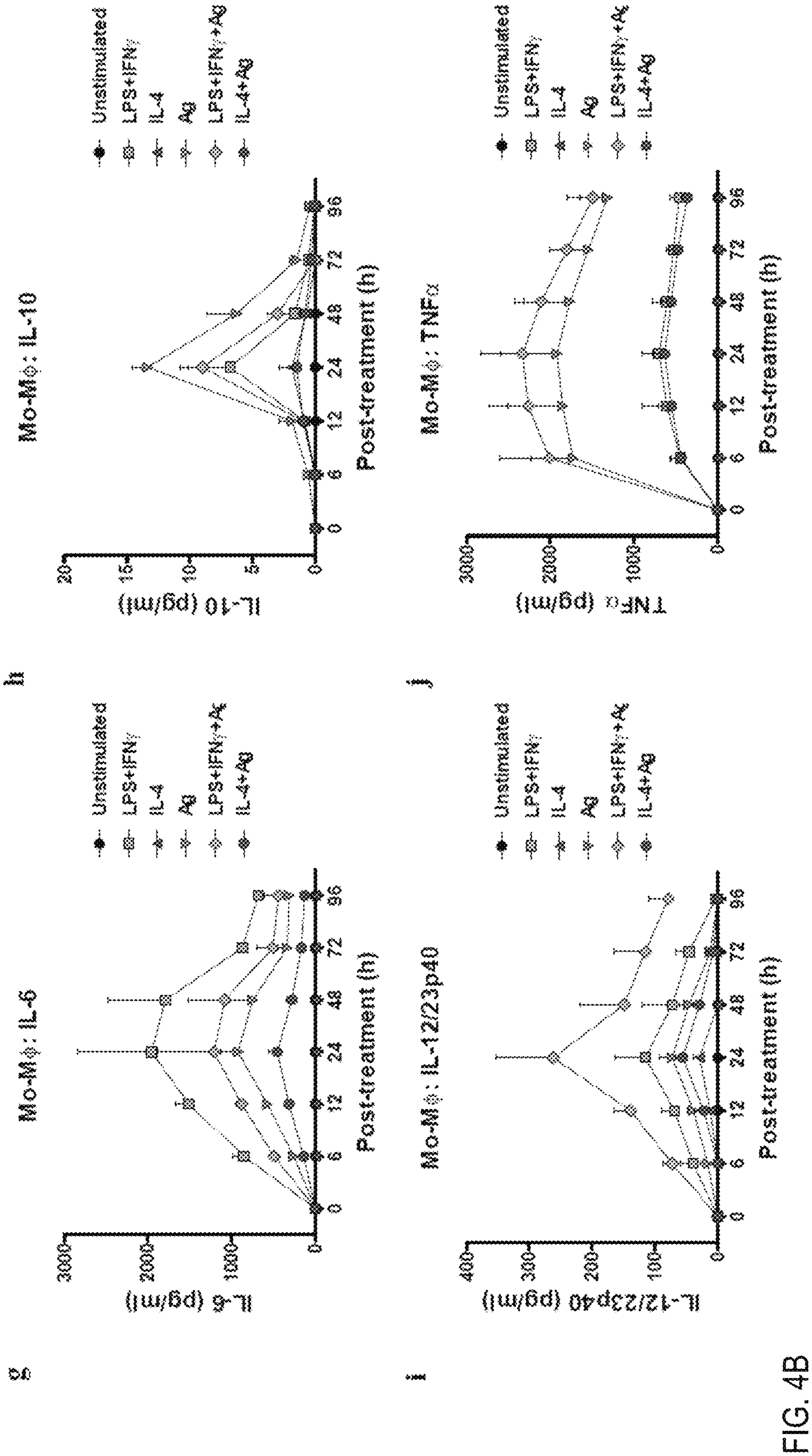

3. PMDV antigen directly stimulates cytokine expression in porcine Mo-DCs and Mo-MΦs In order to investigate the response of APCs in pigs with lower immune responses than cattle, whether or not antigen-mediated cytokines are directly secreted has been identified by polarizing porcine Mo-DCs and Mo-MΦs in monocytes and stimulating the same with O/TWN/97-R antigen. Mo-DCs (a to e in FIG. 4A, Table 2) and/or Mo-MΦs (f in FIG. 4A and g to j in FIG. 4B, Table 3), IL-10, IL-6, IL-12/23p40 (48 h) and TNFα (24 h) expression was reduced after reaching peak levels. O/TWN/97-R antigen induced significantly high levels of expression of these all pro-inflammatory cytokines, whereas IL-10 (anti-inflammatory cytokine) was expressed at low levels in Mo-DCs and Mo-MΦs. In particular, LPS and IFNγ-stimulated M1 MΦs responded more markedly than IL-4-stimulated M2 MΦs.

TABLE 2

| | Mo-DCs | | | | |
|---|---|---|---|---|---|
| Treatment | IL-1β | IL-6 | IL-10 | IL-12/23p40 | TNFα |
| No-stimulation | ND | ND | ND | ND | ND |
| LPS + IFNγ | 2574.67 ± 62.71 | 715.57 ± 144.87 | 22.52 ± 2.83 | 762.33 ± 109.14 | 2578.00 ± 370.16 |
| TNFα | 432.97 ± 15.68 | 201.33 ± 48.09 | 10.85 ± 1.01 | 135.67 ± 28.48 | 74.00 ± 15.82 |
| Ag | 1958.67 ± 201.11 | 277.53 ± 27.67 | 60.58 ± 4.95 | 432.33 ± 39.30 | 2327.00 ± 456.45 |
| LPS + IFNγ + Ag | 3337.67 ± 112.95 | 393.70 ± 42.88 | 11.11 ± 0.80 | 2445.67 ± 487.73 | 3075.67 ± 236.01 |
| TNFα + Ag | 713.93 ± 54.79 | 94.67 ± 13.73 | 69.99 ± 4.75 | 142.33 ± 23.33 | 764.67 ± 224.68 |
| Maximum time point (h) | 48 | 48 | 24 | 48 | 24 |

TABLE 3

| | Mo-MΦs | | | | |
|---|---|---|---|---|---|
| Treatment | IL-1β | IL-6 | IL-10 | IL-12/23p40 | TNFα |
| No stimulation | ND | ND | ND | ND | ND |
| LPS + IFNγ | 1339.00 ± 128.74 | 1959.33 ± 511.82 | 6.80 ± 2.28 | 115.67 ± 27.29 | 700.67 ± 118.75 |
| IL-4 | 223.43 ± 21.45 | ND | 1.88 ± 0.56 | 29.00 ± 5.77 | ND |
| Ag | 1026.30 ± 187.08 | 925.30 ± 119.05 | 13.40 ± 0.67 | 72.33 ± 12.02 | 1920.67 ± 389.75 |

TABLE 3-continued

| | Mo-MΦs | | | | |
|---|---|---|---|---|---|
| Treatment | IL-1β | IL-6 | IL-10 | IL-12/23p40 | TNFα |
| LPS + IFNγ + Ag | 1800.00 ± 57.29 | 1214.83 ± 382.81 | 9.00 ± 0.69 | 262.33 ± 52.07 | 2332.33 ± 288.26 |
| IL-4 + Ag | 100.68 ± 18.31 | 456.57 ± 60.04 | 1.49 ± 0.13 | 55.67 ± 6.67 | 634.33 ± 81.32 |
| Maximum time point (h) | 48 | 24 | 24 | 24 | 24 |

Figure 5A:
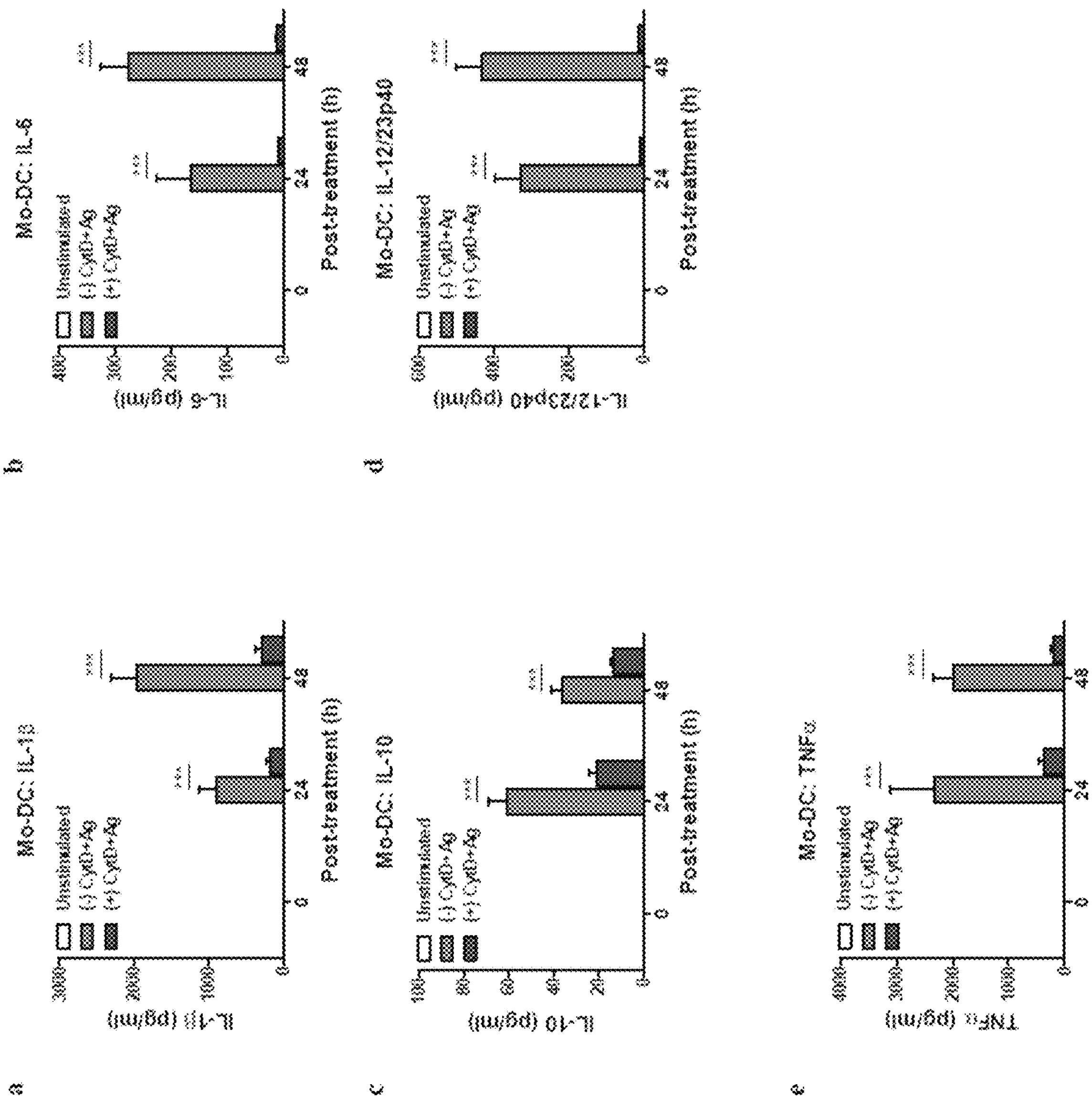
FIGS. 5A and 5B illustrate that FMDV antigen is endocytosed into porcine DCs and MΦs by phagocytosis to initiate cellular immunity.
Figure 5B:
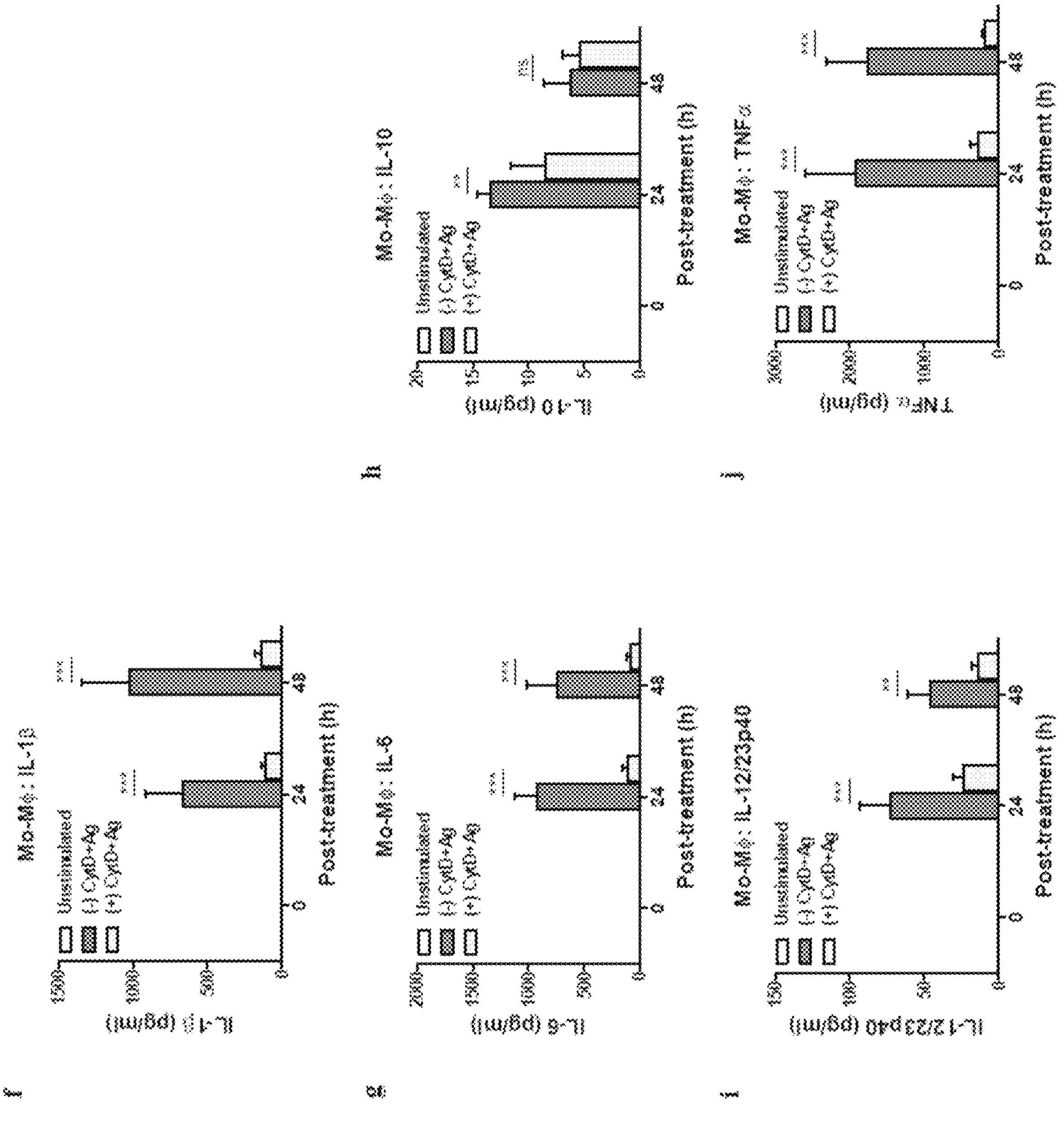

4. FMDV antigen is endocytosed into porcine DCs and MΦs by phagocytosis to initiate cellular immunity. In order to identify a pathway for initiating and amplifying the innate immune response by endocytosis of O/TWN/97-R antigen into porcine Mo-DCs and Mo-MΦs, the cells were treated with antigens and co-cultured before and after treatment of the cells with cytochalasin D (CytD) as an immune suppressor, followed by observing the expression of cytokine in the cell culture (FIGS. 5A and 5B). In Mo-DCs and Mo-MΦs, the expression of cytokine was elevated at 24 h and 48 h after antigen co-culture before CytD treatment, but was significantly suppressed when antigen is co-cultured after CytD treatment. Further, IL-10 expression in Mo-MΦs was slightly suppressed after CytD treatment, but was not significantly different from pretreatment levels.

5. Induction of T Cell Exhaustion Pathway by Abnormally Over-Expressed Innate Immune Response and FMD Vaccine Vaccination in Pigs To elucidate a cause of the lower immune response in pigs compared to cattle, despite antigen-mediated porcine APC stimulation and endocytosis of antigens by phagocytosis on porcine DCs and MΦs, the present inventors have performed RNA-Seq after isolation of naive cattle and pig PBMCs.

Figure 6A:
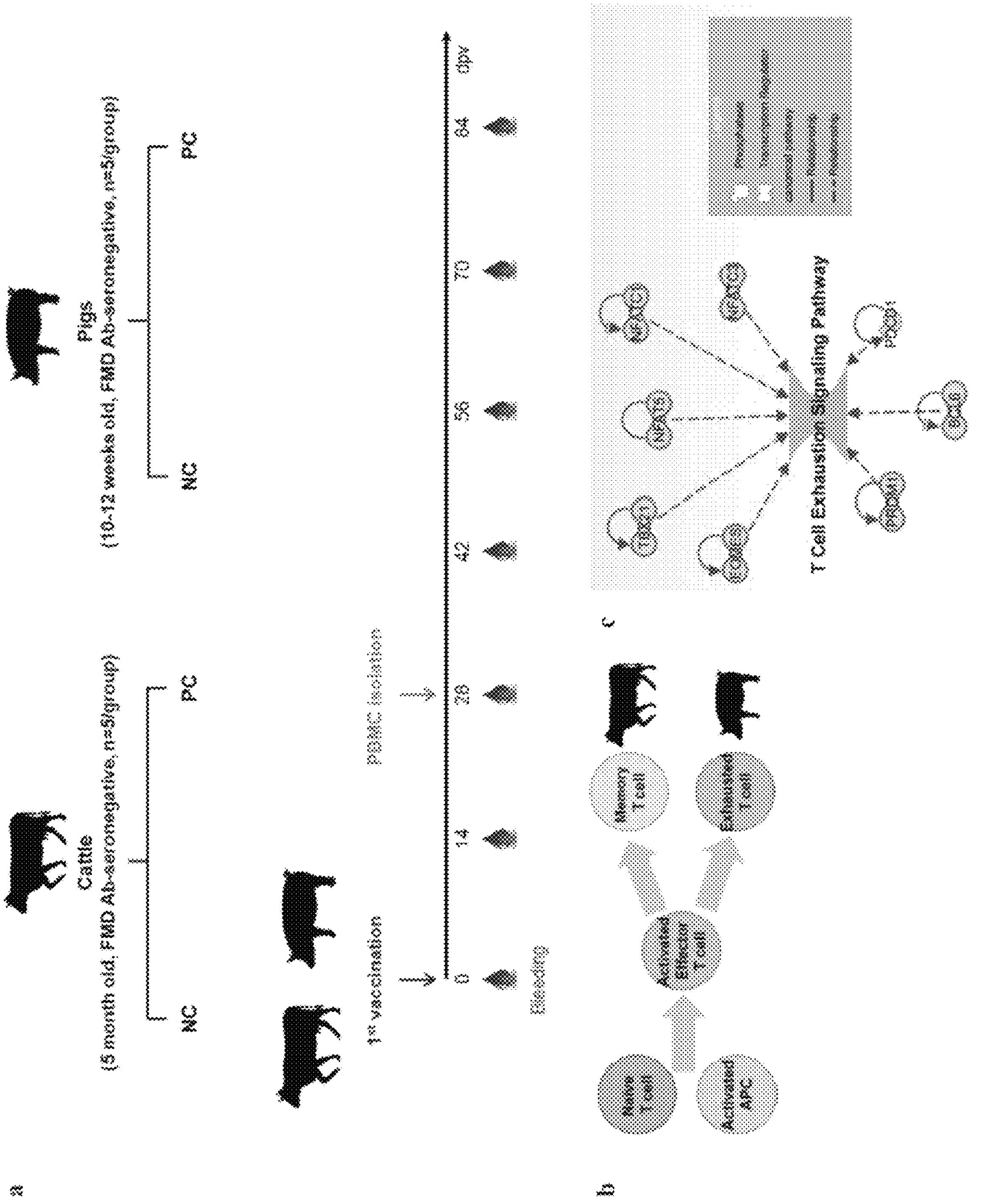
FIG. 6A illustrates an experimental procedure for elucidating a difference in the immune response in cattle and pigs.
Figure 6B:
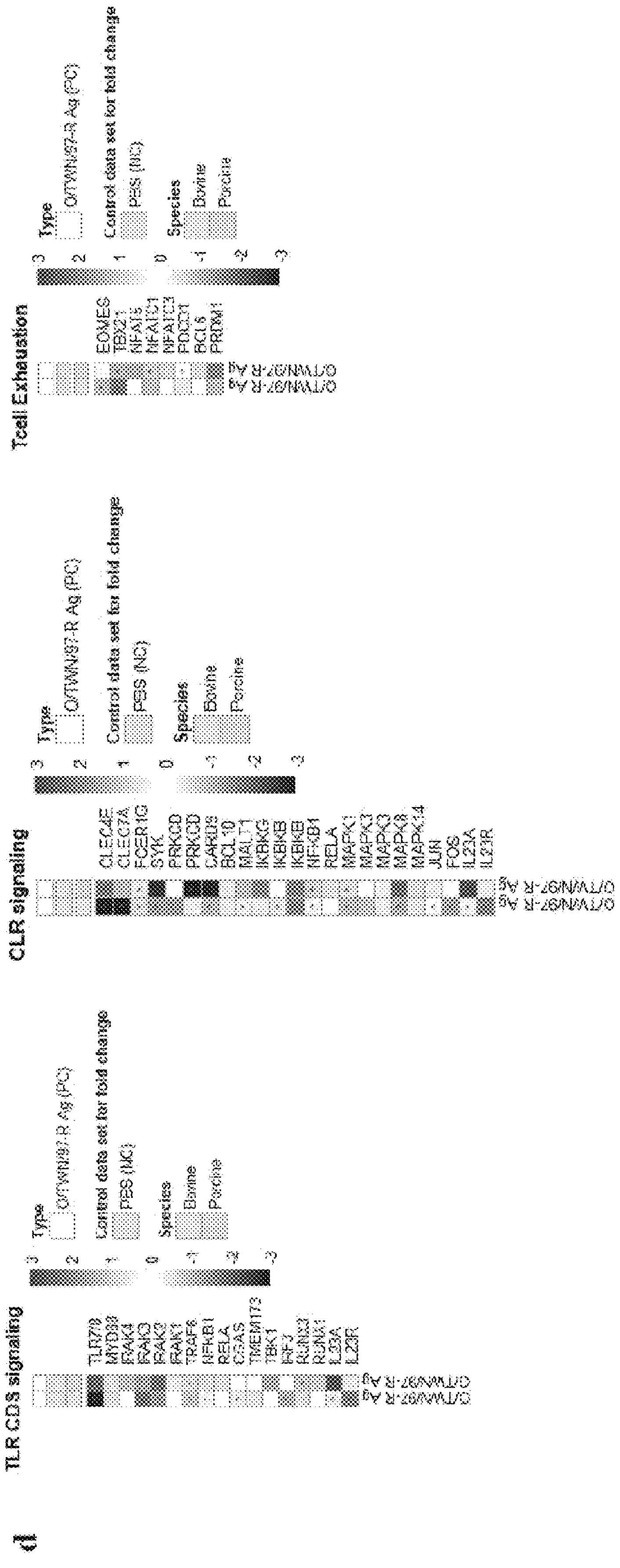
FIGS. 6B and 6C show results of induction of the T cell exhaustion pathway by abnormally over-expressed innate immune response and FMD vaccine vaccination in pigs.
Figure 6C:
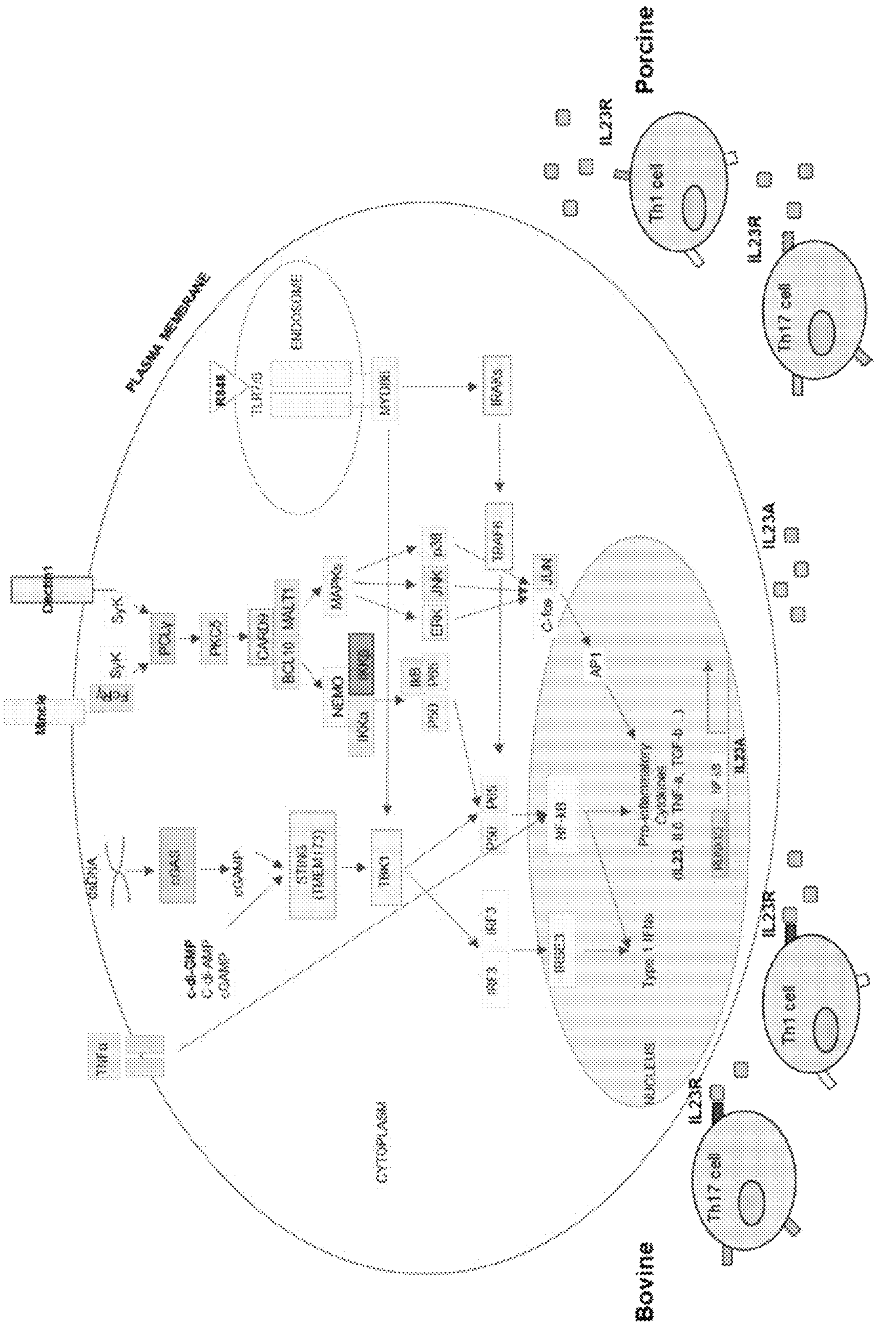

According to the above process, the immune responses of cattle and pigs were compared, and then a fundamental difference in the immune responses between the cattle and pigs, which are induced by FMD vaccination in vivo, was confirmed (FIGS. 6A to 6C). In the natural state, the innate immune response in cattle was well controlled and maintained, whereas it was abnormally over-activated in pigs (b and c in FIG. 6A). Consequently, FMD vaccination induced a normal immune response in livestock, whereas the expression of genes involved in the T cell exhaustion pathway (TBX21, NEAT1, NEAT3, NEAT5, EOMES, PRDM1, BCL6 and PDCD1) was significantly increased in pigs. (FIG. 6B). In particular, according to the analysis of expression of genes involved in TLR/CDS and CLR signaling pathways, it was demonstrated that IL23A and IL23R expression was effectively induced by FMD vaccination in cattle. On the other hand, IL23A showed an over-expression pattern in pigs, however, no IL23R expression was observed (FIG. 6C).

Figure 7A:
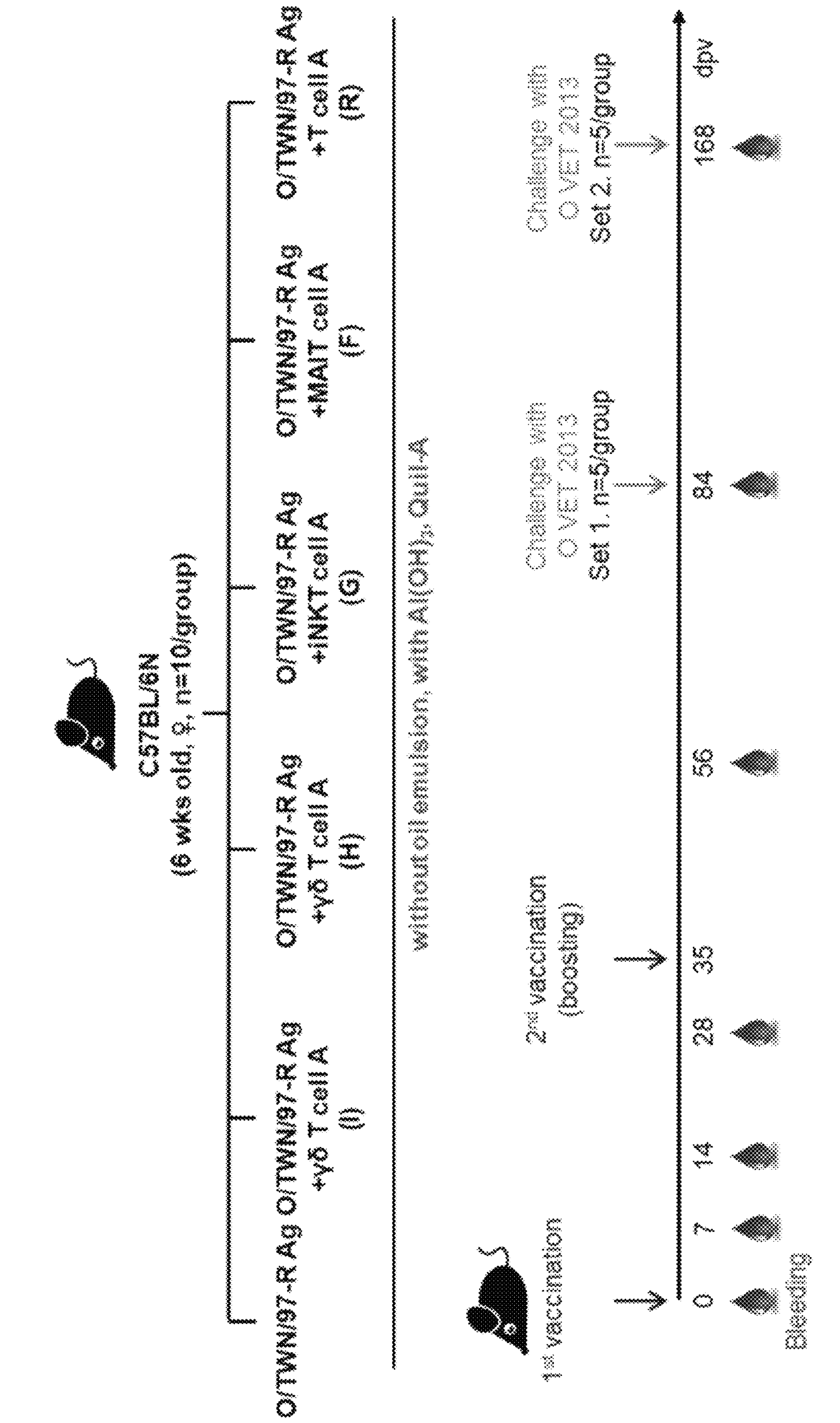
FIG. 7A illustrates the experimental procedure of Experimental Example 1.

<Experimental Example 1> Unconventional T Cell Agonist as an FMD Vaccine Adjuvant Induces Early, Intermediate and Long-Term Immunity in Mice In order to induce a strong cellular immune response by directly activating T cells without stimulating APC, unconventional T cell agonists including γδ T cells, iNKT cells, MAIT cells, as well as conventional T cell agonists as novel FMD vaccine adjuvants were subjected to assessment of availability in mice prior to experiments with pigs as the subject (target) animal. Further, it was evaluated whether there are host protective effects during FMDV infection by efficiently inducing early, intermediate and long-term immune responses even in the vaccine without oil emulsion (FIG. 7A).

Figure 7B:
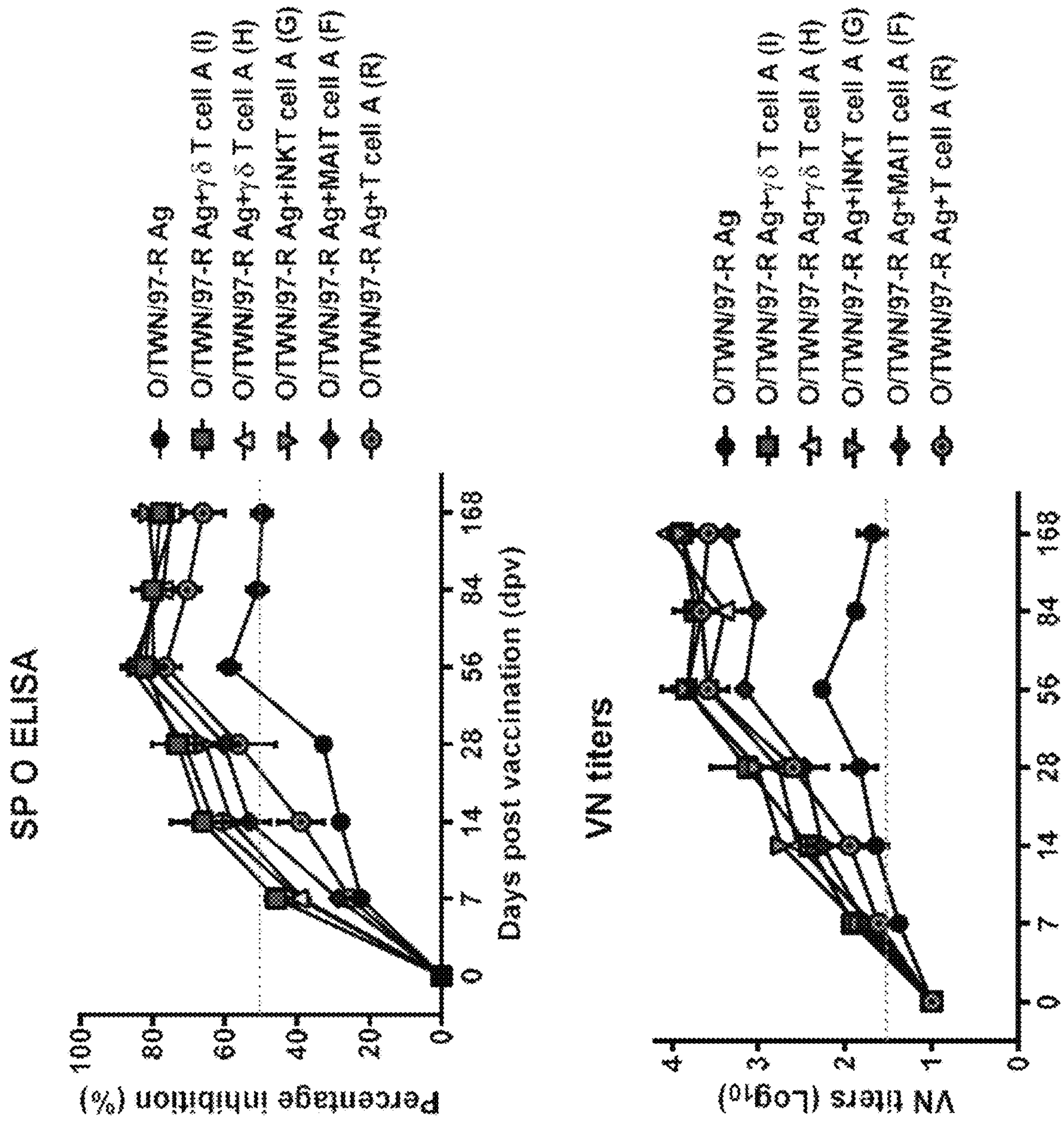
FIGS. 7B to 7D show results of confirming that unconventional T cell agonists and conventional T cell agonists induce early, intermediate and long-term immunity in mice.

Compared to the control, antibody titers measured by SP-O ELISA were significantly higher at 7 days post-vaccination (dpv) after administration of γδ T cell agonists (isopentyl pyrophosphate trilithium salt, IPP (I)), (E)-1-hydroxy-2-methyl-2-butenyl 4-pyrophosphate lithium salt, HMP (H)) and iNKT cell agonist (α-galactosylceramide, α-Gal (G)). The titers were also increased in the group administered with MAIT cell agonists (6-formylprine, 6-Formylpterin (F)) at 14 dpv. With respect to the conventional T cell agonist (RORγT(R)), the antibody titer was similar to that of the unconventional T cell agonist at 28 dpv. Further, the antibody titers in all experimental groups were significantly higher than those of the control up to at 168 dpv (FIG. 7B).

Figure 7C:
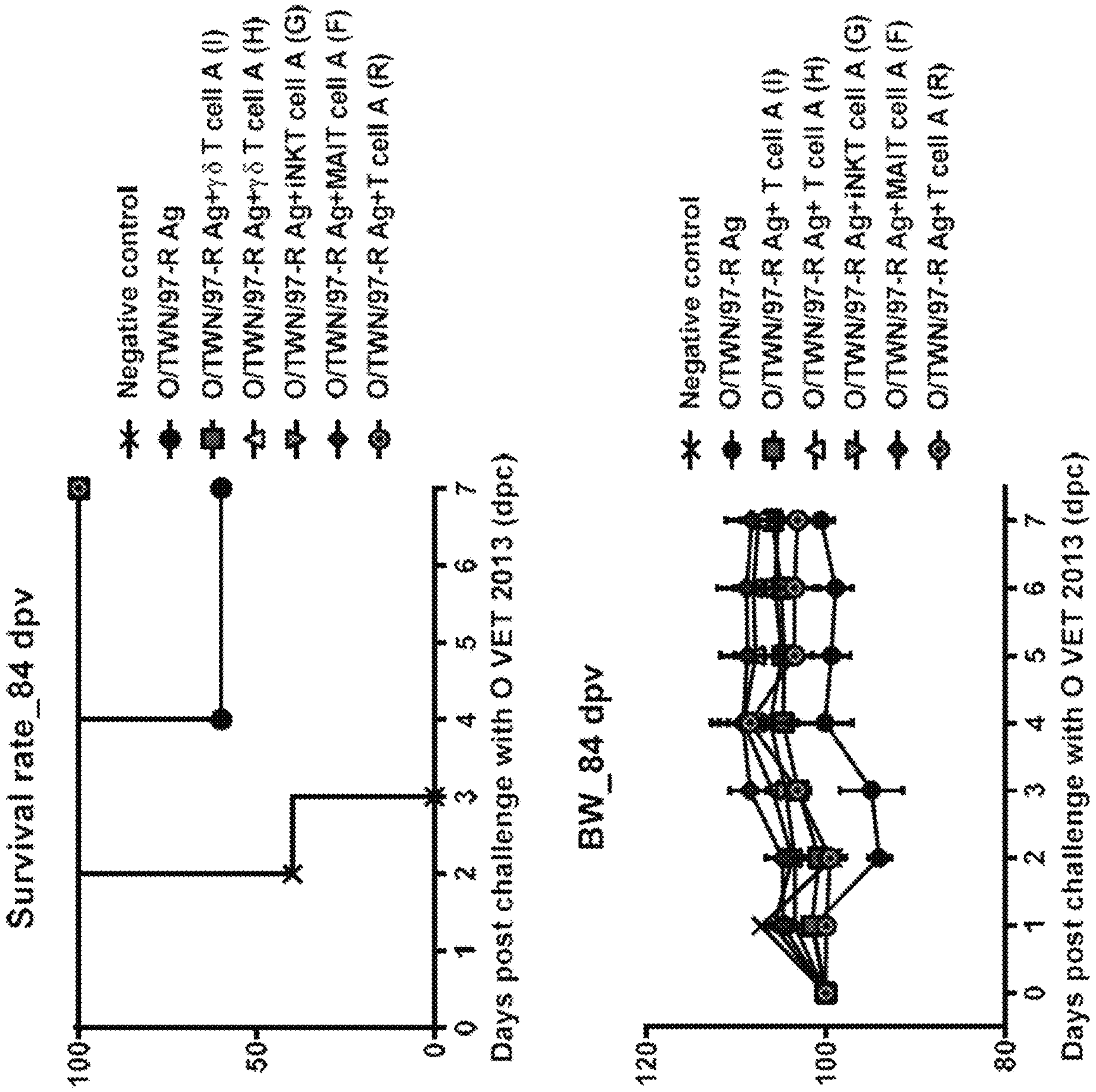
Figure 7D:
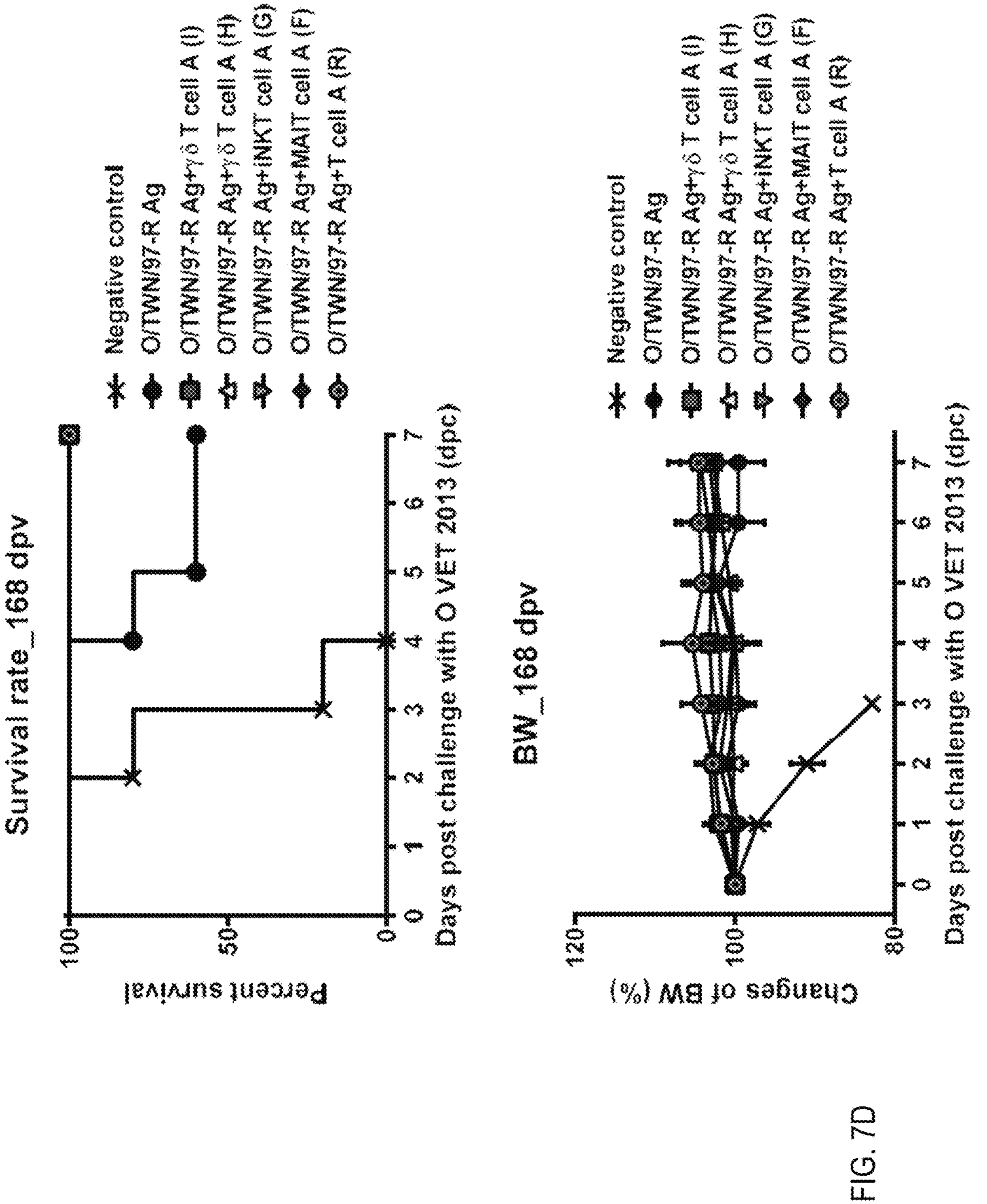

Virus neutralization (VN) titers showed a similar trend to antibody titers by SP-O ELISA. The neutralizing antibody of the γδ T cell agonist (I)-, γδ T cell agonist (H)- and iNKT cell agonist (G)-administered groups increased approximately 100-fold at 7 dpv, while high levels of VN titers were also seen at 14 dpv in the MAIT cell agonist (F)-administered group. At 28 dpv, the VN titers were highest in the γδ T cell agonist (I)- and iNKT cell agonist (G)-administered groups. VN titers peaked at 56 dpv after boosting, and all unconventional T cell agonist-administered groups maintained significantly higher neutralizing antibody titers than the control at 168 dpv (FIG. 7B). The FMDV (O/VET/2013 of 100 $LD_{50}$) challenge test at 84 and 168 dpv showed 100% survival (FIG. 7C) in all adjuvant treatment groups, with very little body weight change (FIG. 7D).

Therefore, it was confirmed that FMD vaccines containing unconventional T cell agonists have potent effects on the induction of early, intermediate and long-term immunity in mice.

Figure 8A:
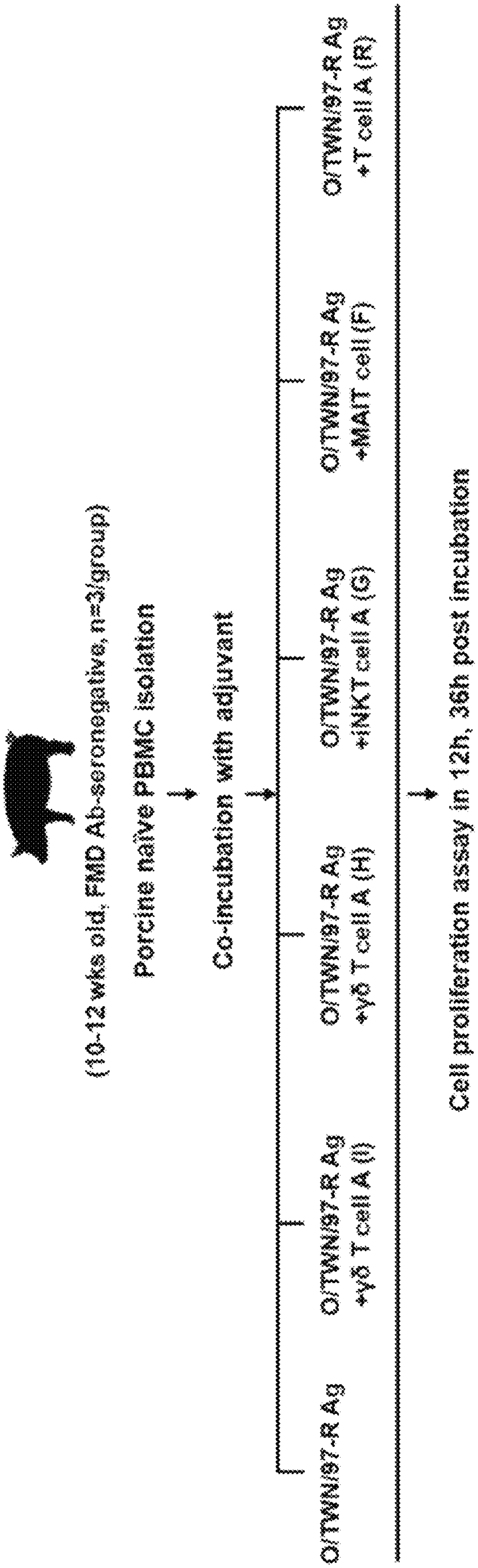
FIG. 8A illustrates an experimental procedure of Experimental Example 2.
Figure 8B:
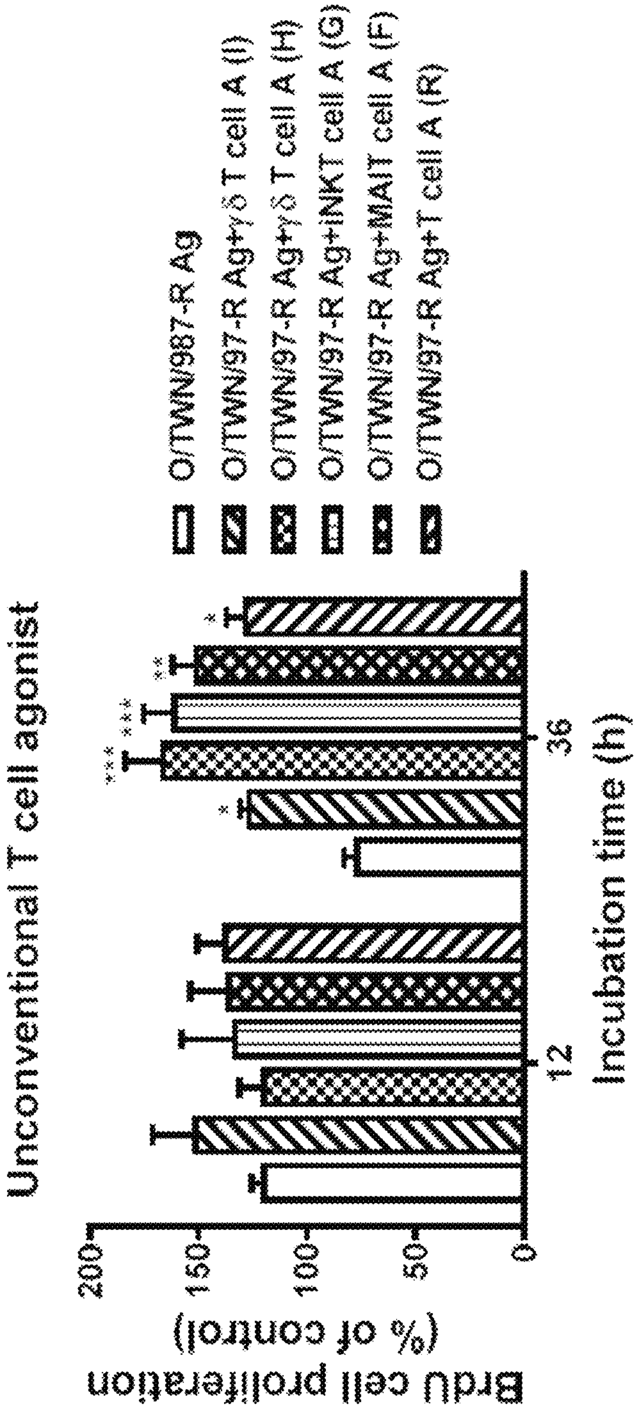
FIG. 8B shows results of cell proliferation in T cell agonist-induced porcine PBMCs.
Figure 9A:
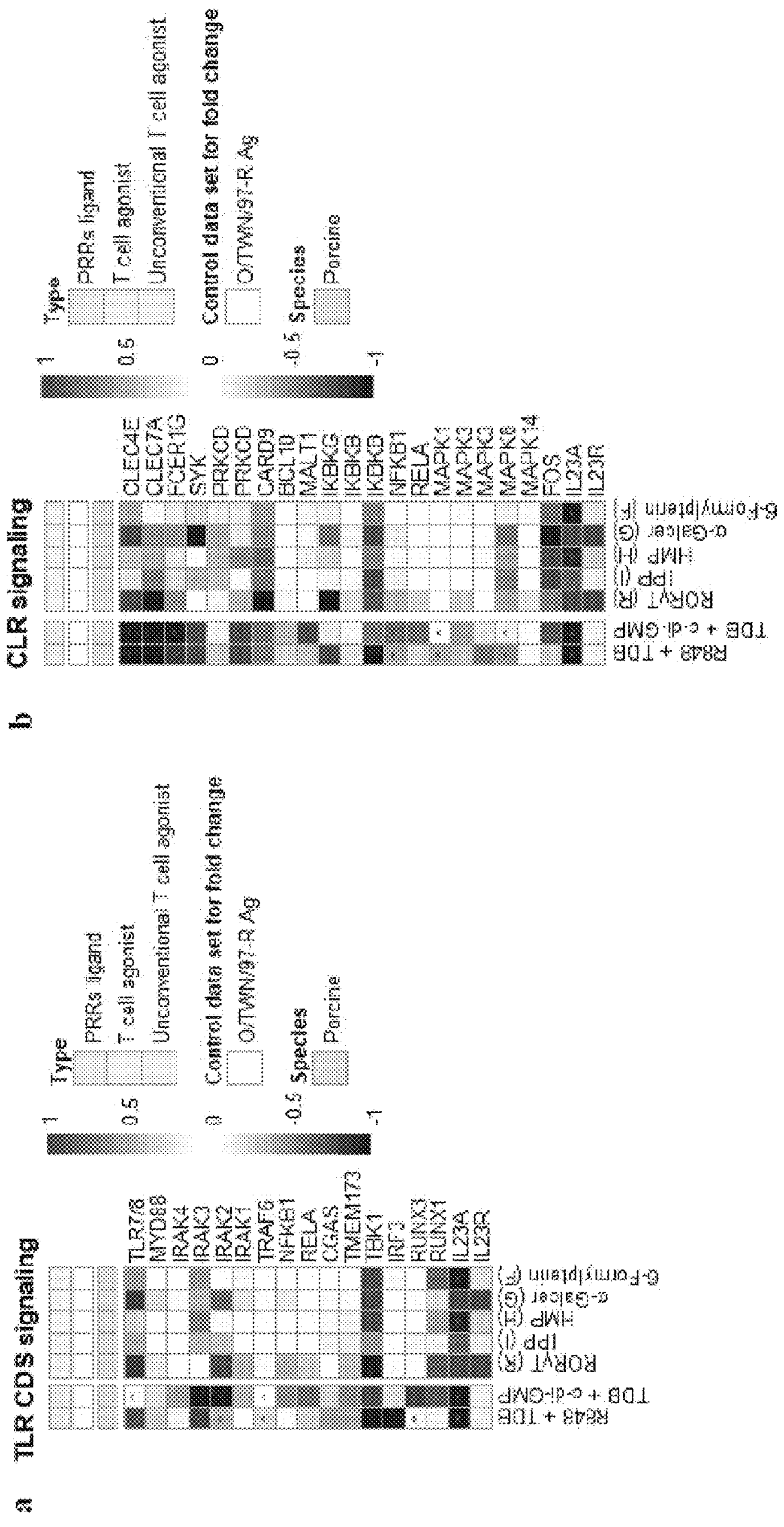
FIGS. 9A to 9E show results of Experimental Example 3, wherein unconventional T cell agonist and conventional T cell agonist of Experimental Example 3 improve the abnormal innate immune response and activate of immune cells including T cells in pigs.
Figure 9A:
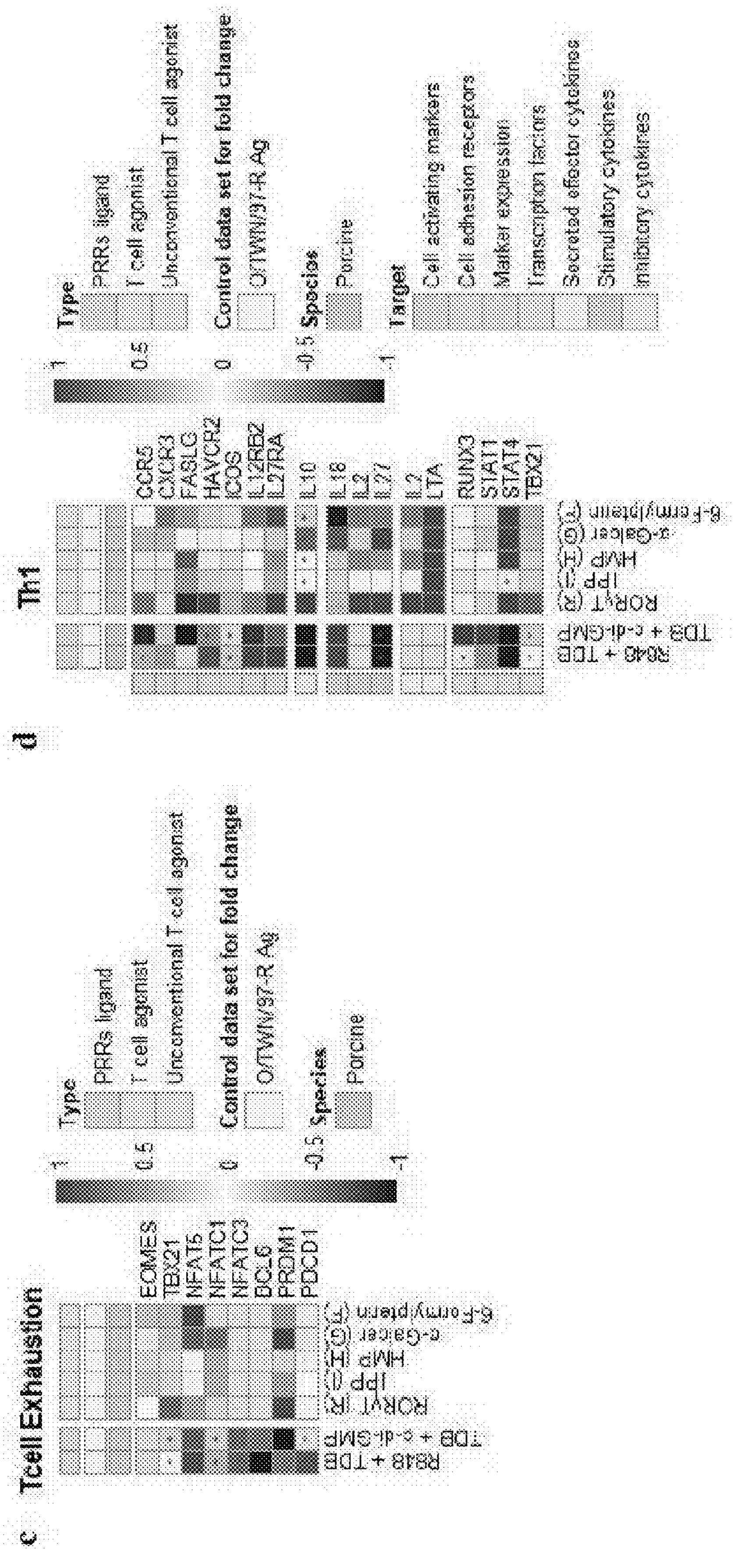
Figure 9B:
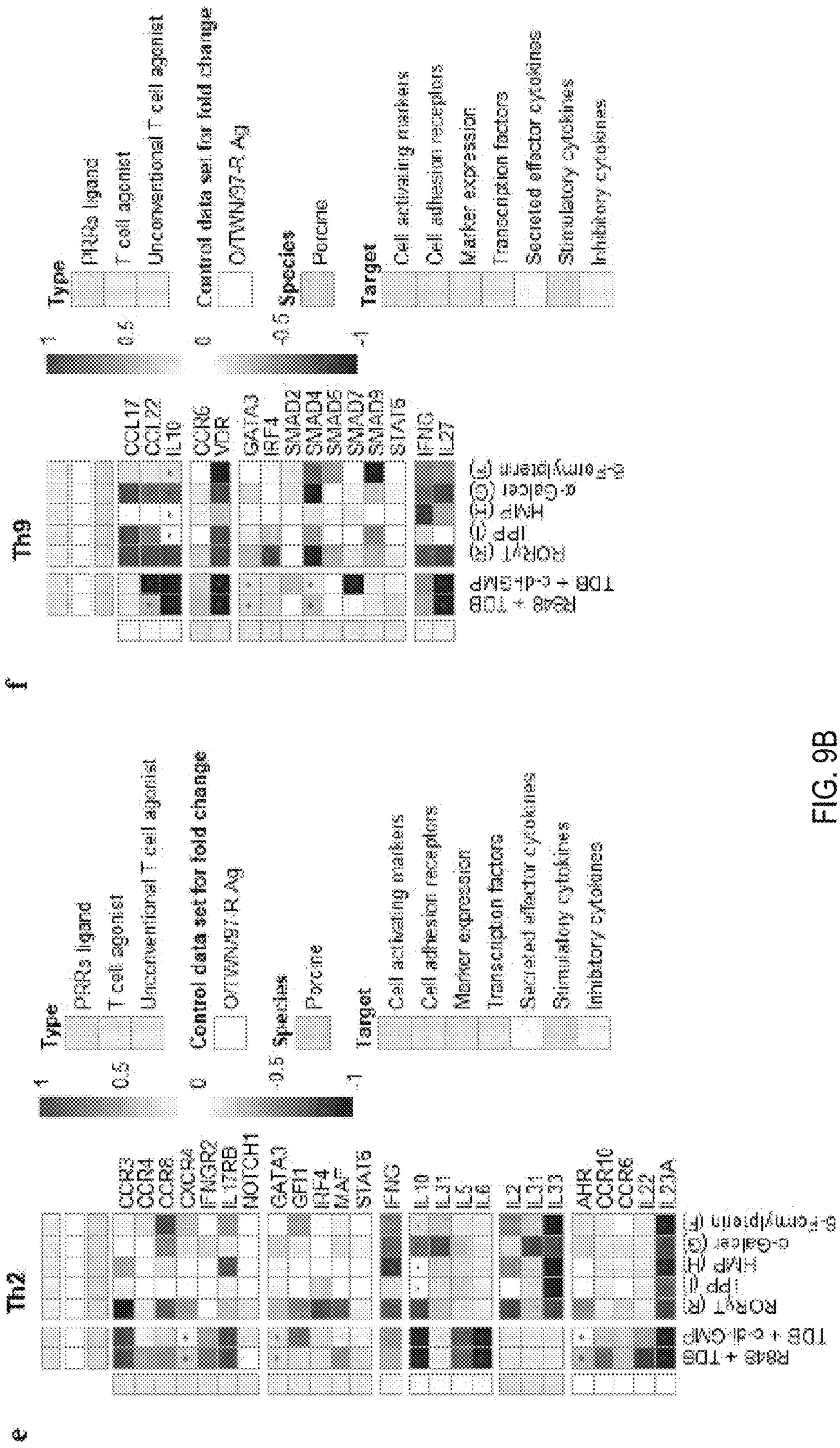
Figure 9B:
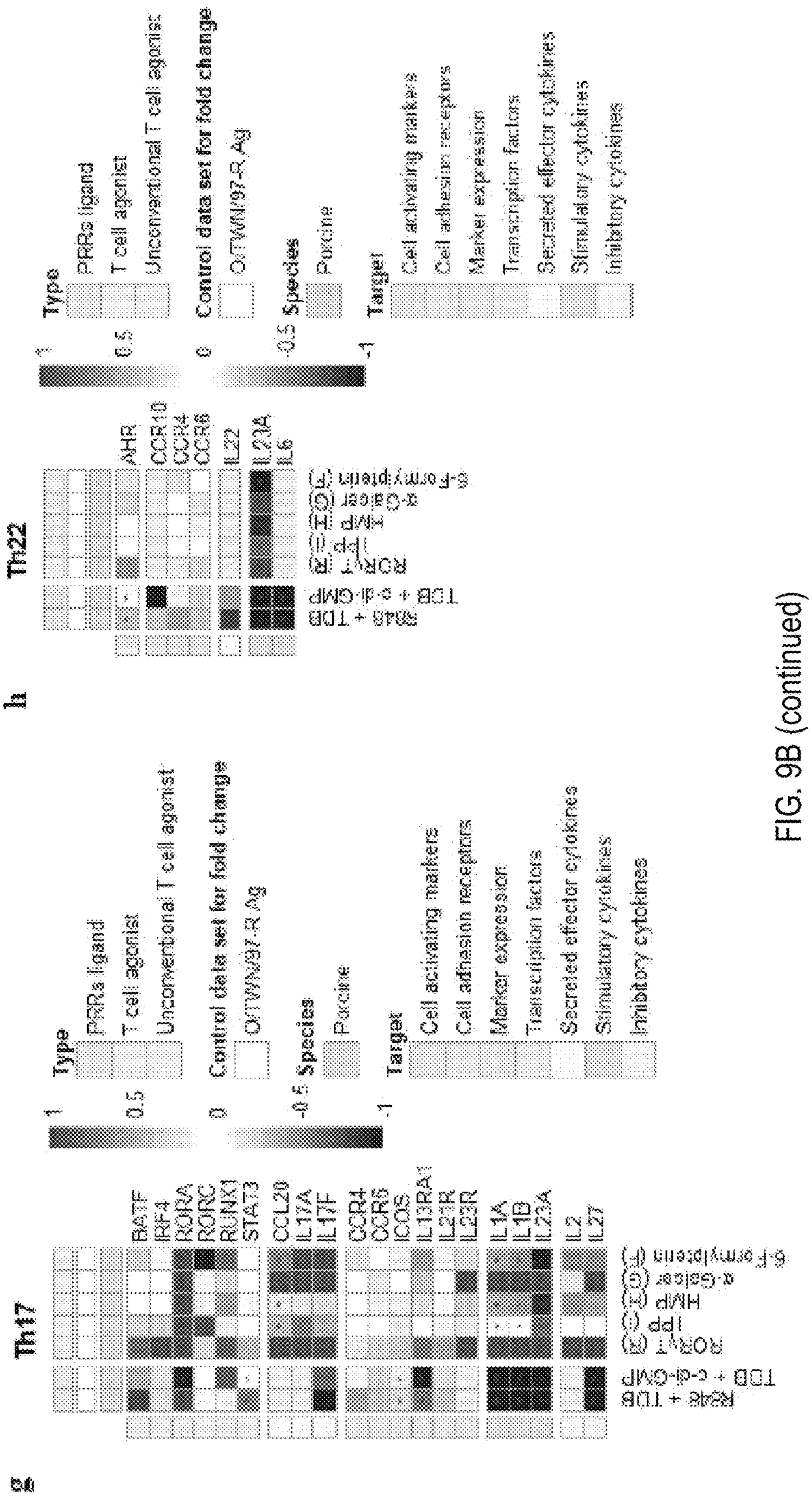
Figure 9C:
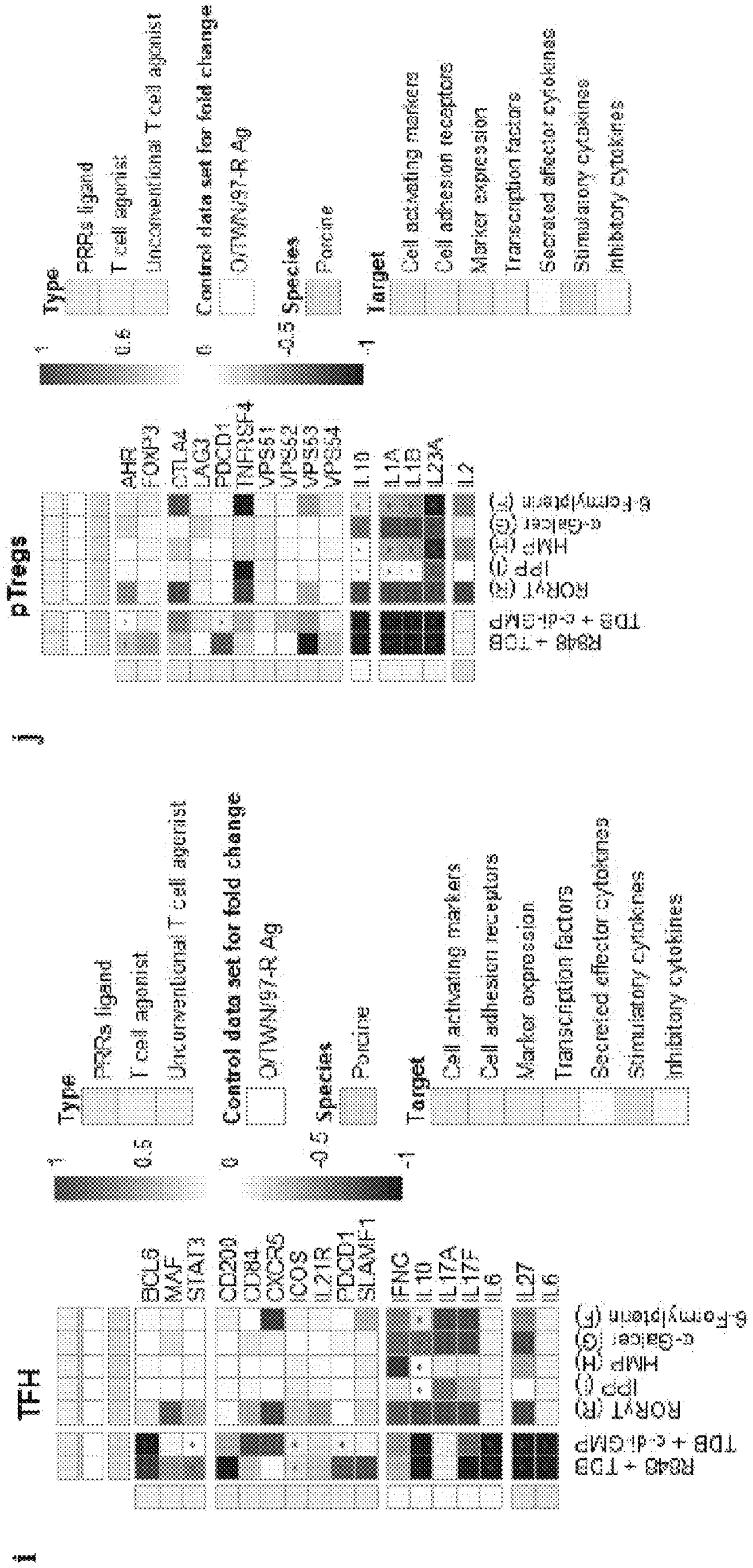
Figure 9C:
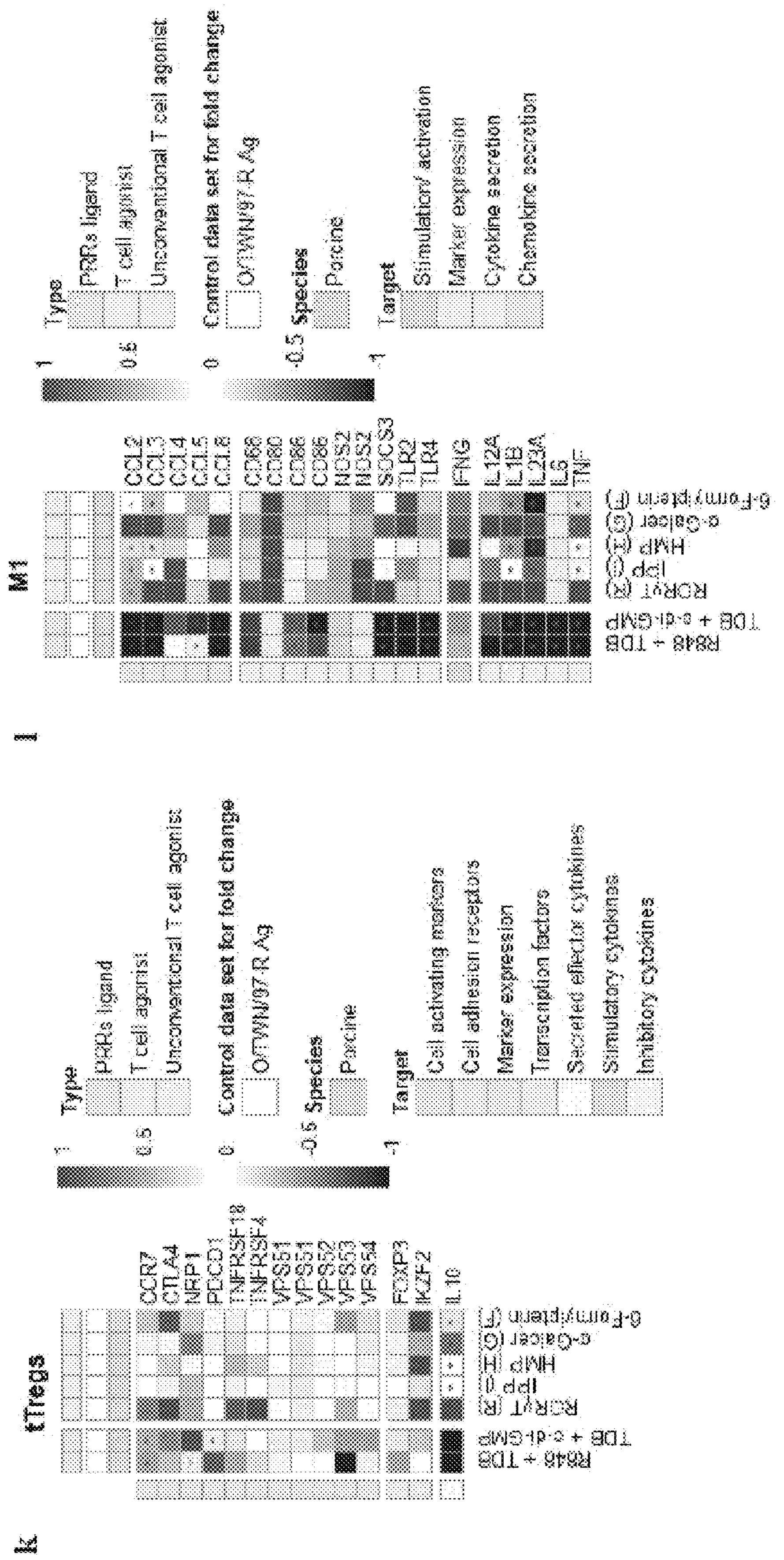
Figure 9D:
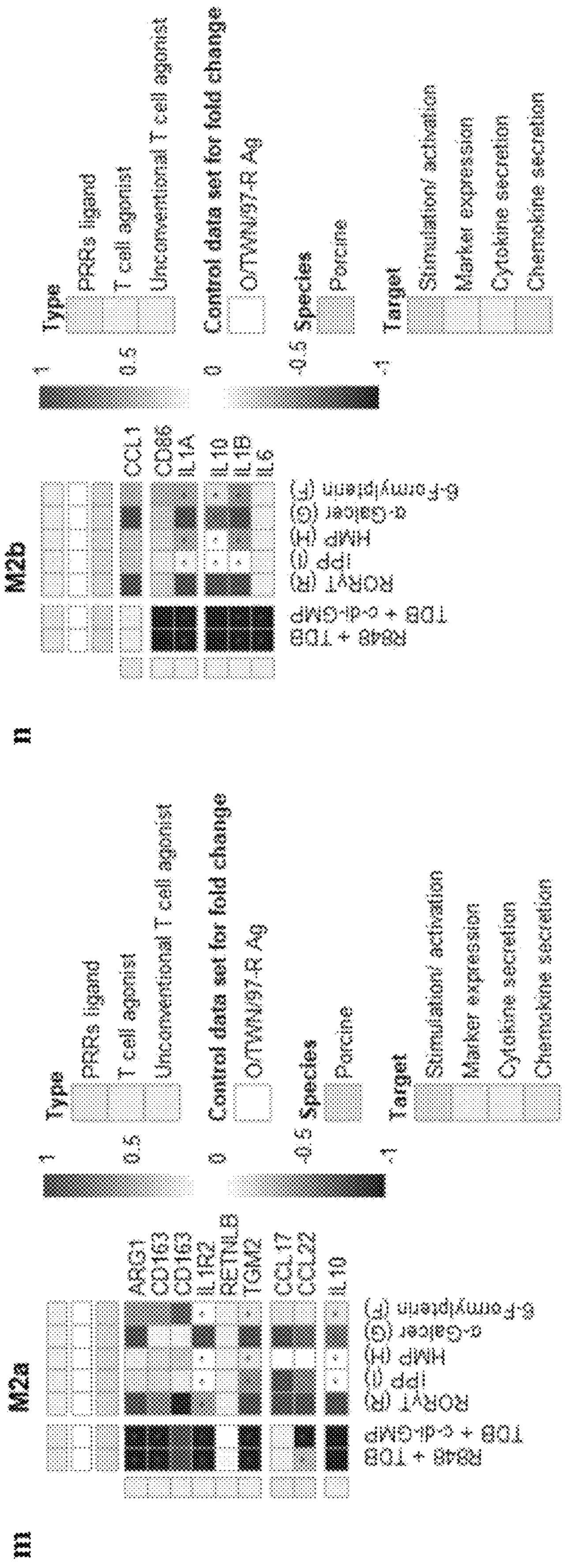
Figure 9E:
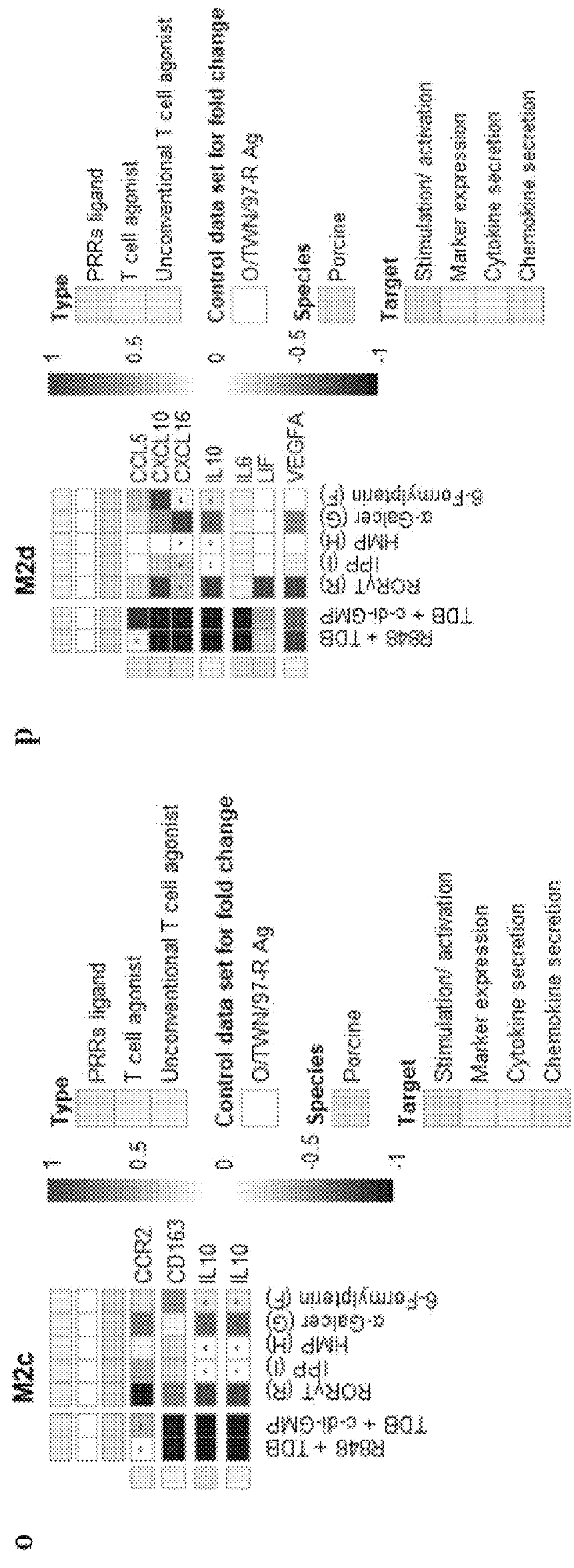
Figure 9E:
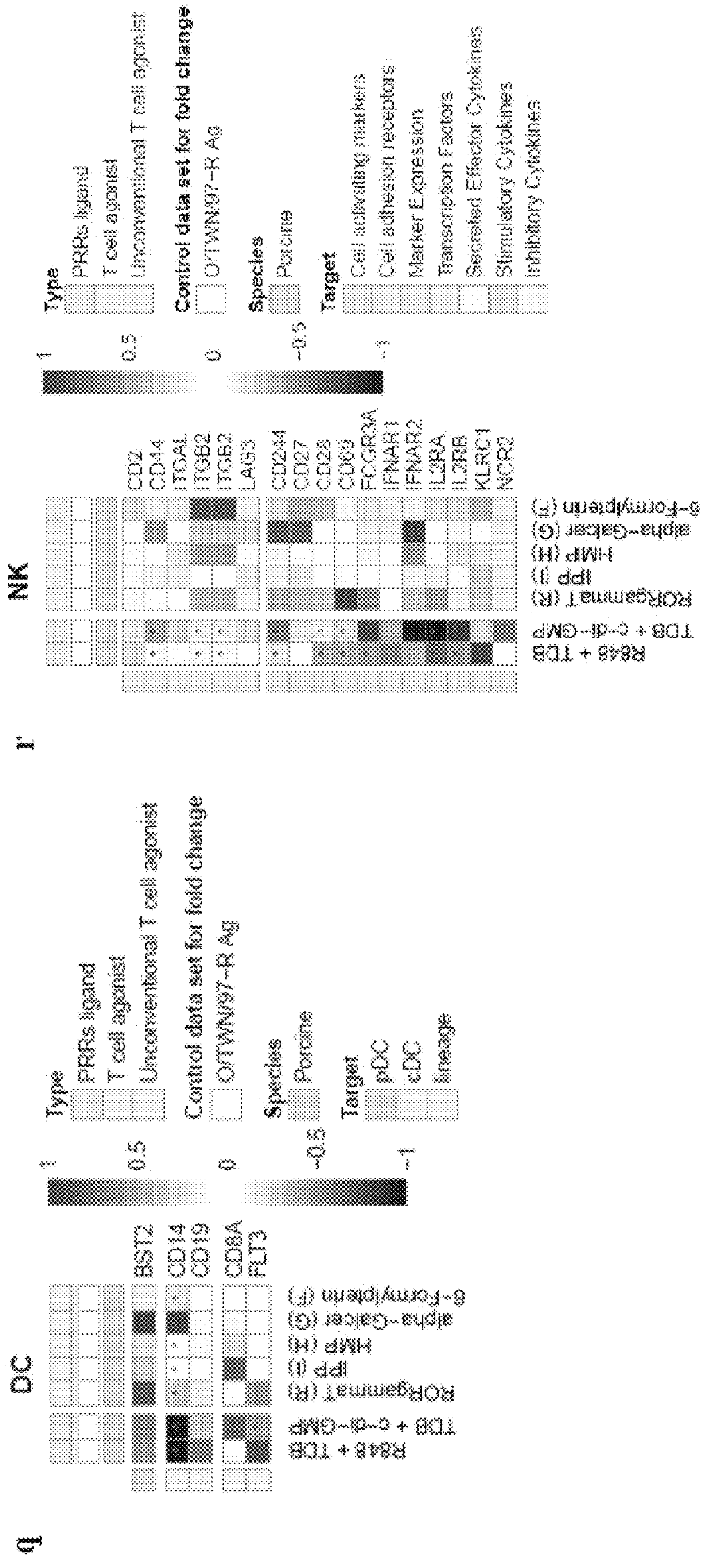

<Experimental Example 2> Unconventional T Cell Agonist Induces Strong Cell Proliferation of Porcine PBMCs Unconventional T cell agonist-mediated cell proliferation was observed in porcine naive PBMCs isolated from FMD antibody-negative producing animals at 12 and 36 hours after incubation (FIG. 8A). To provide conditions similar to the actual test vaccine, the FMD serotype 0 (0/TWN/97-R) antigen was co-administered with the unconventional T cell agonist. Cell proliferation was high in the following order: antigen+γδ T cell agonist (H)>antigen+iNKT cell agonist (G)>antigen+MAIT cell agonist (F)>antigen+T cell agonist (R)>antigen+γδ T cell agonist (I)>antigen alone (FIG. 8B).

<Experimental Example 3> Unconventional T Cell Agonist Improves Abnormal Innate Immune Response in Pigs and Directly Activates T Cells which Induce a Strong Immune Response without APC Stimulation In order to overcome low immunogenicity compared to cattle by inducing a strong cellular immune response in pigs and to provide solutions to various problems posed in pigs, a system for indirectly activating T cells by stimulating APCs such as DCs and MΦs with PRRs ligands thus to induce an immune response was compared with another system which induces an immune response by directly stimulating T cells through unconventional T cell agonist and T cell agonist. Naive PBMCs were isolated from FMD antibody-negative pigs, and then, antigen+PRR ligand (resiquimod (R848, TLR-7/8 agonist) and trehalose-6, 6-divehenate (TDB, Mincle agonist); TDB and bis-(3'-5')-cyclic dimer guanosine monophosphate (c-di-GMP, STING agonist) or antigen+unconventional T cell agonist (γδ T cell agonist, I; γδ T cell agonist, H; iNKT cell agonist, G; MAIT cell agonist, F or antigen+T cell agonist, R, or antigen alone, respectively, were used for treatment, PBMCs were collected after 12 hours, total RNA was extracted using TRIzol Reagent (Invitrogen) and RNeasy Mini Kit (QIAGEN) according to the manufacturer's recommended method, followed by performing RNA-Seq, thereby confirming the induction of an adjuvant-mediated cellular immune response and related gene expression profile (FIGS. 9A to 9E).

Gene expression profiles relevant to TLR/CDS signaling showed that PRR ligands induced TLR-7/8, cGAS and RUNX3 expression. Further, it was confirmed that the conventional unconventional T cell agonists significantly affected TBK1, RUNX1, IL23A and IL23R expression (a in FIG. 9A). The CLR signaling pathway was significantly induced by treatment with the conventional T cell agonists, compared to PRR ligand treatment. Further, IL23A and IL23R were specifically highly expressed in the iNKT cell agonist (G)-treated groups among the unconventional T cell agonists, as well as the conventional T cell agonist (R)-treated groups (b in FIG. 9A). Further, T cell exhaustion pathway-related gene expression was improved by treatment with PRR ligands and the unconventional T cell agonist (c in FIG. 9A). Gene expression in Th1, Th2, Th9, Th17, Th22, Tfh, pTreg and tTreg cells was significantly increased in the groups treated with the unconventional T cell agonist and the conventional T cell agonist, compared to the PRR ligand-treated group. Further, IL23A and IL23R expressions were also enhanced, while LTA, STAT4, CCL17, CCL22, IL10, RORA, CCL20, IL17A, IL17F, IL1α and IL1β expressions were also increased by T cell agonist treatment (d in FIG. 9A, e to h in FIG. 9B, and i to k in FIG. 9C). Notably, gene expression in M1, M2a, M2b, M2c, M2d and DCs was significantly enhanced by treatment with unconventional T cell agonists and conventional T cell agonists compared with APC-stimulated PRR ligand treatment. Further, the expression of CD80, CD86, CCL1, CCL2, CCL3, CCL17, CCL22, IL1β, IL23A, TNFα, IL1R2, TGM2, CXCL10, CXCL16 and CD14 was significantly increased (1 in FIG. 9C, m and n in FIG. 9D, and o to q in FIG. 9E). In addition, it was observed that ITGB2 and IFNAR2 gene expression in NK cells was increased by treatment with unconventional T cell agonists and T cell agonists (r in FIG. 9E)

ACKNOWLEDGEMENT INFORMATION

Assignment Identification Number: 1545019609

Assignment Number: B-153386-2019-21-03

Project management organization name: Agriculture, Forestry and Livestock Quarantine Headquarters Research business project name: Development of quarantine inspection technology for agriculture, forestry and livestock Research project name: Establishment of a next-generation swine foot-and-mouth disease vaccine platform capable of inducing non-oil type long-term immunity

The invention claimed is:

1. A foot-and-mouth disease (FMD) vaccine composition comprising an adjuvant composition, wherein the adjuvant composition comprises any one or more selected from the group consisting of γδ T cell agonist, MAIT cell agonist, and T cell agonist, as an active ingredient, wherein the γδ T cell agonist is isopentenyl pyrophosphate trilithium salt;

wherein the MAIT cell agonist is 6-formylpterin;

wherein the T cell agonist is RORγT.

2. The vaccine composition according to claim 1, wherein the active ingredient is included in an amount of 0.01 to 1% by weight based on a total weight of the adjuvant composition.

3. The vaccine composition according to claim 1, further comprising additives, excipients, and/or carriers in addition to the active ingredient.

4. The vaccine composition according to claim 1, wherein the adjuvant composition has the form of an oil preparation or a non-oil preparation.

5. The vaccine composition according to claim 1, wherein the adjuvant composition is included in an amount of 30 to 70% by weight based on a total weight of the vaccine composition.

* * * * *